US010517976B2

(12) United States Patent
Shur et al.

(10) Patent No.: US 10,517,976 B2
(45) Date of Patent: *Dec. 31, 2019

(54) ULTRAVIOLET SYSTEM FOR DISINFECTION

(71) Applicant: Sensor Electronic Technology, Inc., Columbia, SC (US)

(72) Inventors: Michael Shur, Vienna, VA (US); Maxim S. Shatalov, Columbia, SC (US); Timothy James Bettles, Irmo, SC (US); Yuri Bilenko, Columbia, SC (US); Alexander Dobrinsky, Silver Spring, MD (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/856,978

(22) Filed: Dec. 28, 2017

(65) Prior Publication Data

US 2018/0140726 A1    May 24, 2018

Related U.S. Application Data

(63) Continuation of application No. 15/388,506, filed on Dec. 22, 2016, now Pat. No. 9,878,061, which is a
(Continued)

(51) Int. Cl.
*A61L 2/10* (2006.01)
*A23L 3/28* (2006.01)
(Continued)

(52) U.S. Cl.
CPC .............. *A61L 2/10* (2013.01); *A23L 3/003* (2013.01); *A23L 3/28* (2013.01); *A61L 2/24* (2013.01);
(Continued)

(58) Field of Classification Search
CPC .......... A23L 3/003; A23L 3/28; A23L 3/3409; A61L 2/10; A61L 2/24
See application file for complete search history.

(56) References Cited

U.S. PATENT DOCUMENTS 2,482,507 A * 9/1949 Rentschler .............. A23C 3/07
426/248
3,817,703 A    6/1974 Atwood
(Continued)

FOREIGN PATENT DOCUMENTS

CN    1269246 A    10/2000
CN    2488020 Y    4/2002
(Continued)

OTHER PUBLICATIONS

Martin, E., U.S. Appl. No. 15/670,750, Non-Final Rejection, dated Mar. 15, 2018, 62 pages.
(Continued)

*Primary Examiner* — Wyatt A Stoffa
(74) *Attorney, Agent, or Firm* — LaBatt, LLC

(57) ABSTRACT

Ultraviolet radiation is directed within an area. The target wavelength ranges and/or target intensity ranges of the ultraviolet radiation sources can correspond to at least one of a plurality of selectable operating configurations including a sterilization operating configuration and a preservation operating configuration.

20 Claims, 13 Drawing Sheets

Related U.S. Application Data continuation-in-part of application No. 14/937,090, filed on Nov. 10, 2015, now Pat. No. 9,707,307.

(51) Int. Cl.
| | |
|---|---|
| *A61L 2/24* | (2006.01) |
| *F25D 11/00* | (2006.01) |
| *F25D 17/04* | (2006.01) |
| *A23L 3/00* | (2006.01) |
| *A61L 2/28* | (2006.01) |
| *A61L 2/18* | (2006.01) |

(52) U.S. Cl.
CPC .............. *A61L 2/28* (2013.01); *F25D 11/00* (2013.01); *F25D 17/042* (2013.01); *A23V 2002/00* (2013.01); *A61L 2/18* (2013.01); *A61L 2202/11* (2013.01); *A61L 2202/14* (2013.01); *A61L 2202/18* (2013.01); *A61L 2202/23* (2013.01); *F25D 2317/0417* (2013.01); *F25D 2400/361* (2013.01); *F25D 2700/06* (2013.01)

(56) References Cited

U.S. PATENT DOCUMENTS

| | | | |
|---|---|---|---|
| 4,736,416 | A | 4/1988 | Weinert |
| 4,857,277 | A | 8/1989 | Broomfield |
| 4,867,052 | A | 9/1989 | Cipelletti |
| 5,078,971 | A | 1/1992 | Matuda et al. |
| 5,117,642 | A | 6/1992 | Nakanishi et al. |
| 5,136,170 | A | 8/1992 | Gellert |
| 5,230,220 | A | 7/1993 | Kang et al. |
| 5,364,645 | A | 11/1994 | Lagunas-Solar et al. |
| 5,454,944 | A | 10/1995 | Clack |
| 5,768,898 | A | 6/1998 | Seok et al. |
| 5,836,669 | A | 11/1998 | Hed |
| 5,865,959 | A | 2/1999 | Meinzer et al. |
| 5,889,684 | A | 3/1999 | Ben-David et al. |
| 5,901,564 | A | 5/1999 | Comeau, II |
| 5,919,422 | A | 7/1999 | Yamanaka et al. |
| 6,165,526 | A | 12/2000 | Newman |
| 6,182,453 | B1 | 2/2001 | Forsberg |
| 6,312,608 | B1 | 11/2001 | Buckner |
| 6,447,721 | B1 | 9/2002 | Horton, III et al. |
| 6,471,136 | B1* | 10/2002 | Chatterjee ............ F25D 17/042 237/2 B |
| 6,477,853 | B1 | 11/2002 | Khorram |
| 6,524,529 | B1 | 2/2003 | Horton, III |
| 6,565,803 | B1 | 5/2003 | Bolton et al. |
| 6,574,984 | B1 | 6/2003 | McCrea et al. |
| 6,576,188 | B1 | 6/2003 | Rose et al. |
| 6,579,495 | B1 | 6/2003 | Maiden |
| 6,592,816 | B1 | 7/2003 | Ebel et al. |
| 6,673,137 | B1 | 1/2004 | Wen |
| 6,735,479 | B2 | 5/2004 | Fabian et al. |
| 6,818,177 | B1 | 11/2004 | Turcotte |
| 6,878,761 | B2 | 4/2005 | Gugumus |
| 7,026,018 | B2 | 4/2006 | Kranovich |
| 7,160,370 | B2 | 1/2007 | Baca et al. |
| 7,296,422 | B2 | 11/2007 | Strohm et al. |
| 7,323,065 | B2 | 1/2008 | Fencl et al. |
| 7,401,469 | B2* | 7/2008 | Joshi ................... A23L 3/3445 236/91 C |
| 7,452,561 | B2* | 11/2008 | Newman ................ A23B 7/015 426/248 |
| 7,634,996 | B2 | 12/2009 | Gaska et al. |
| 7,645,381 | B2 | 1/2010 | Oranski et al. |
| 7,754,156 | B2 | 7/2010 | Hyde et al. |
| 7,897,104 | B2* | 3/2011 | Kwon ................ A47L 15/0013 134/58 D |
| 8,062,589 | B2 | 11/2011 | Naarup |
| 8,114,342 | B2 | 2/2012 | Jung et al. |
| 8,178,042 | B2 | 5/2012 | Jung et al. |
| 8,277,734 | B2 | 10/2012 | Koudymov et al. |
| 8,384,047 | B2 | 2/2013 | Shur et al. |
| 8,828,315 | B2* | 9/2014 | Ryska .................... A23B 7/015 422/306 |
| 9,006,680 | B2 | 4/2015 | Bettles et al. |
| 9,042,967 | B2 | 5/2015 | Dacosta et al. |
| 9,061,082 | B2 | 6/2015 | Gaska et al. |
| 9,138,499 | B2 | 9/2015 | Bettles et al. |
| 9,179,703 | B2* | 11/2015 | Shur .................... A23L 3/003 |
| 9,572,903 | B2 | 2/2017 | Dobrinsky et al. |
| 9,603,960 | B2 | 3/2017 | Dobrinsky et al. |
| 9,687,577 | B2 | 6/2017 | Dobrinsky et al. |
| 9,707,307 | B2* | 7/2017 | Shur ...................... A61L 2/10 |
| 9,718,706 | B2 | 8/2017 | Smetona et al. |
| 9,724,441 | B2 | 8/2017 | Shur et al. |
| 9,750,830 | B2 | 9/2017 | Shur et al. |
| 9,757,486 | B2 | 9/2017 | Dobrinsky et al. |
| 9,801,965 | B2 | 10/2017 | Bettles et al. |
| 9,802,840 | B2 | 10/2017 | Shturm et al. |
| 9,878,061 | B2* | 1/2018 | Shur ...................... A61L 2/28 |
| 2002/0063954 | A1 | 5/2002 | Horton, III |
| 2002/0074559 | A1 | 6/2002 | Dowling et al. |
| 2002/0122743 | A1 | 9/2002 | Huang |
| 2002/0176809 | A1 | 11/2002 | Siess |
| 2003/0019222 | A1 | 1/2003 | Takahashi et al. |
| 2003/0019505 | A1 | 1/2003 | Scheir et al. |
| 2003/0164754 | A1* | 9/2003 | Roseen ................... F25D 25/00 340/309.16 |
| 2003/0194692 | A1 | 10/2003 | Purdum |
| 2004/0018125 | A1 | 1/2004 | Yang et al. |
| 2004/0210099 | A1 | 10/2004 | Shiratori |
| 2005/0165499 | A1* | 7/2005 | Stein ..................... A23B 7/152 700/83 |
| 2005/0178977 | A1* | 8/2005 | Koenck ................. A23B 4/015 250/455.11 |
| 2005/0186124 | A1 | 8/2005 | Fink et al. |
| 2005/0217282 | A1* | 10/2005 | Strohm .................. A23B 7/152 62/78 |
| 2005/0257827 | A1 | 11/2005 | Gaudiana et al. |
| 2005/0274965 | A1 | 12/2005 | Phillips et al. |
| 2006/0091310 | A1 | 5/2006 | Furry |
| 2006/0130498 | A1 | 6/2006 | Joshi et al. |
| 2006/0147339 | A1 | 7/2006 | Hunter et al. |
| 2006/0163169 | A1 | 7/2006 | Eckhardt et al. |
| 2006/0216193 | A1 | 9/2006 | Johnson et al. |
| 2006/0237687 | A1 | 10/2006 | Yue et al. |
| 2007/0051901 | A1 | 3/2007 | Hopaluk et al. |
| 2007/0104841 | A1* | 5/2007 | Min ...................... A23L 3/005 426/248 |
| 2007/0164232 | A1 | 7/2007 | Rolleri et al. |
| 2007/0172560 | A1 | 7/2007 | Mirtsching et al. |
| 2007/0172661 | A1 | 7/2007 | Fechner et al. |
| 2007/0196235 | A1* | 8/2007 | Shur ...................... A23L 3/28 422/62 |
| 2007/0205382 | A1* | 9/2007 | Gaska .................... A61L 2/10 250/504 R |
| 2007/0248487 | A1* | 10/2007 | Kay ....................... C02F 1/325 422/24 |
| 2007/0295203 | A1 | 12/2007 | Shekarriz et al. |
| 2008/0061005 | A1 | 3/2008 | Hopaluk et al. |
| 2008/0067418 | A1 | 3/2008 | Ross |
| 2008/0168788 | A1 | 7/2008 | Hurlebaus et al. |
| 2008/0168790 | A1 | 7/2008 | Hurlebaus et al. |
| 2008/0213129 | A1* | 9/2008 | van der Pol .............. A61L 2/10 422/24 |
| 2008/0286146 | A1 | 11/2008 | Schroll et al. |
| 2008/0295033 | A1* | 11/2008 | Lee ....................... F25D 23/126 715/840 |
| 2008/0307818 | A1 | 12/2008 | Min et al. |
| 2009/0110933 | A1 | 4/2009 | Hyde et al. |
| 2009/0185960 | A1* | 7/2009 | Busujima ................ A61L 2/208 422/116 |
| 2009/0228155 | A1 | 9/2009 | Slifkin et al. |
| 2009/0229287 | A1 | 9/2009 | Prentner |
| 2009/0280035 | A1* | 11/2009 | Koudymov .............. A23L 3/28 422/108 |
| 2010/0065632 | A1 | 3/2010 | Babcock et al. |
| 2010/0097013 | A1 | 4/2010 | Inskeep |

(56) References Cited

U.S. PATENT DOCUMENTS

| | | | |
|---|---|---|---|
| 2010/0101432 A1* | 4/2010 | Biotti | A23L 3/3418 99/473 |
| 2010/0227031 A1 | 9/2010 | Vasilenko | |
| 2010/0296971 A1* | 11/2010 | Gaska | A61L 2/10 422/62 |
| 2010/0307973 A1 | 12/2010 | Grcevic | |
| 2011/0030560 A1 | 2/2011 | Bohlen et al. | |
| 2011/0044848 A1 | 2/2011 | Wright | |
| 2011/0147617 A1* | 6/2011 | Shur | A01G 7/045 250/461.1 |
| 2011/0163046 A1 | 7/2011 | Neal et al. | |
| 2011/0228534 A1 | 9/2011 | Zhang et al. | |
| 2011/0297241 A1* | 12/2011 | Biotti | A23L 3/3418 137/14 |
| 2011/0306262 A1 | 12/2011 | Arpin | |
| 2012/0011874 A1 | 1/2012 | Conradt et al. | |
| 2012/0017628 A1 | 1/2012 | Okabe et al. | |
| 2012/0025104 A1 | 2/2012 | Park et al. | |
| 2012/0051030 A1 | 3/2012 | Johnson | |
| 2012/0085116 A1* | 4/2012 | Maeng | F25D 17/042 62/264 |
| 2012/0104021 A1 | 5/2012 | Cur et al. | |
| 2012/0126134 A1 | 5/2012 | Deal et al. | |
| 2013/0015753 A1 | 1/2013 | Son et al. | |
| 2013/0048545 A1 | 2/2013 | Shatalov et al. | |
| 2013/0337121 A1* | 12/2013 | Sugano | A23B 4/015 426/232 |
| 2014/0042012 A1 | 2/2014 | Clement et al. | |
| 2014/0060094 A1* | 3/2014 | Shur | A61L 2/10 62/129 |
| 2014/0060095 A1* | 3/2014 | Shur | A61L 2/10 62/129 |
| 2014/0060104 A1* | 3/2014 | Shur | A61L 2/10 62/264 |
| 2014/0102127 A1* | 4/2014 | Yum | F25D 29/00 62/340 |
| 2014/0202962 A1 | 7/2014 | Bilenko et al. | |
| 2014/0209928 A1 | 7/2014 | Teng et al. | |
| 2015/0161909 A1* | 6/2015 | Won | G06F 19/3475 434/127 |
| 2015/0165079 A1 | 6/2015 | Shur et al. | |
| 2015/0297767 A1 | 10/2015 | Gaska et al. | |
| 2015/0336810 A1 | 11/2015 | Smetona et al. | |
| 2016/0000953 A1 | 1/2016 | Bettles et al. | |
| 2016/0058020 A1 | 3/2016 | Shur et al. | |
| 2016/0114186 A1 | 4/2016 | Dobrinsky et al. | |
| 2016/0281959 A1 | 9/2016 | Khizar et al. | |
| 2016/0324996 A1 | 11/2016 | Bilenko et al. | |
| 2017/0057842 A1 | 3/2017 | Dobrinsky et al. | |
| 2017/0071332 A1 | 3/2017 | Herring et al. | |
| 2017/0100494 A1 | 4/2017 | Dobrinsky et al. | |
| 2017/0100495 A1 | 4/2017 | Shur et al. | |
| 2017/0100496 A1 | 4/2017 | Shur et al. | |
| 2017/0189711 A1 | 7/2017 | Shur et al. | |
| 2017/0245527 A1 | 8/2017 | Dobrinsky et al. | |
| 2017/0245616 A1 | 8/2017 | Lakios et al. | |
| 2017/0281812 A1 | 10/2017 | Dobrinsky et al. | |
| 2017/0368215 A1 | 12/2017 | Shatalov et al. | |
| 2018/0117194 A1 | 5/2018 | Dobrinsky et al. | |
| 2018/0243458 A1 | 8/2018 | Shatalov et al. | |

FOREIGN PATENT DOCUMENTS

| | | |
|---|---|---|
| CN | 1580626 A | 2/2005 |
| CN | 101171938 A | 5/2008 |
| CN | 101322000 A | 12/2008 |
| CN | 102389579 A | 3/2012 |
| CN | 202236462 U | 5/2012 |
| CN | 102564003 A | 7/2012 |
| CN | 103550799 A | 2/2014 |
| EP | 1038536 B1 | 6/2005 |
| JP | 2002204653 A | 7/2002 |
| KR | 1020090074966 A | 7/2009 |
| KR | 1020110057773 A | 6/2011 |
| KR | 1020120011458 A | 2/2012 |
| WO | 2013/096243 A1 | 6/2013 |
| WO | 2014036137 A1 | 3/2014 |

OTHER PUBLICATIONS

Zhou, Z., Application No. 201380053729.9, Office Action2 (with English translation), dated Jan. 29, 2018, 13 pages.

Mayekar, K., U.S. Appl. No. 14/012,682, Notice of Allowance, dated Jan. 22, 2015, 16 pages.

Mayekar, K., U.S. Appl. No. 14/012,682, Non-Final Rejection, dated Sep. 24, 2014, 20 pages.

Mayekar, K., U.S. Appl. No. 14/629,508, Notice of Allowance, dated Nov. 16, 2017, 22 pages.

Mayekar, K., U.S. Appl. No. 14/629,508, Non-Final Rejection, dated Jun. 13, 2017, 74 pages.

Martin, E., U.S. Appl. No. 14/012,667, Notice of Allowance, dated Jun. 16, 2017, 25 pages.

Martin, E., U.S. Appl. No. 14/012,667, Final Rejection2, dated Nov. 30, 2016, 25 pages.

Martin, E., U.S. Appl. No. 14/012,667, Non-Final Rejection2, dated Jun. 28, 2016, 20 pages.

Martin, E., U.S. Appl. No. 14/012,667, Final Rejection 1, dated Apr. 1, 2016, 15 pages.

Martin, E., U.S. Appl. No. 14/012,667, Non-Final Rejection, dated Dec. 3, 2015, 73 pages.

Martin, E., U.S. Appl. No. 14/541,245, Notice of Allowance, dated Apr. 3, 2017, 18 pages.

Martin, E., U.S. Appl. No. 14/541,245, Final Rejection 1, dated Nov. 28, 2016, 23 pages.

Martin, E., U.S. Appl. No. 14/541,245, Non-Final Rejection 1, dated Jun. 17, 2016, 60 pages.

Mendoza-Wilkenfe, E., U.S. Appl. No. 14/012,652, Notice of Allowance, dated Mar. 10, 2017, 37 pages.

Mendoza-Wilkenfe, E., U.S. Appl. No. 14/012,652, Final Rejection, dated Nov. 17, 2016, 22 pages.

Mendoza-Wilkenfe, E., U.S. Appl. No. 14/012,652, Non-Final Rejection, dated Jun. 1, 2016, 74 pages.

Stoffa, W., U.S. Appl. No. 14/012,644, Notice of Allowance, dated Jul. 9, 2015, 32 pages.

Stoffa, W., U.S. Appl. No. 14/012,644, Notice of Allowance, dated Apr. 1, 2015, 15 pages.

Stoffa, W., U.S. Appl. No. 14/012,644, Non-Final Rejection, dated Oct. 21, 2014, 19 pages.

Stoffa, W., U.S. Appl. No. 14/012,644, Final Rejection, dated Jul. 3, 2014, 18 pages.

Stoffa, W., U.S. Appl. No. 14/012,644, Non-Final Rejection, dated Mar. 10, 2014, 30 pages.

Stoffa, W., U.S. Appl. No. 14/937,090, Notice of Allowance, dated Mar. 2, 2017, 18 pages.

Stoffa, W., U.S. Appl. No. 14/937,090, Final Rejection, dated Oct. 27, 2016, 45 pages.

Stoffa, W., U.S. Appl. No. 14/937,090, Non-Final Rejection, dated Jun. 1, 2016, 45 pages.

Stoffa, W., U.S. Appl. No. 15/388,506, Notice of Allowance, dated Sep. 6, 2017, 35 pages.

Stoffa, W., U.S. Appl. No. 15/388,506, Non-Final Rejection, dated Apr. 12, 2017, 51 pages.

Cox, A., U.S. Appl. No. 14/012,637, Non-Final Rejection, dated Jun. 29, 2017, 35 pages.

Cox, A., U.S. Appl. No. 14/012,637, Final Rejection, dated Feb. 2, 2017, 33 pages.

Cox, A., U.S. Appl. No. 14/012,637, Final Rejection1 (updated to Non-Final Rejection dated Nov. 18, 2016), dated Aug. 25, 2016, 27 pages.

Cox, A., U.S. Appl. No. 14/012,637, Non-Final Rejection, dated Feb. 19, 2016, 49 pages.

Zhou, Z., Application No. 201380056459.7, Notice of Allowance (There is no English translation available.), dated Mar. 13, 2018, 2 pages.

果品蔬菜保鲜技术和设备 (Google translation of title: "Fruit and vegetable preservation technology and equipment"), 2 pages.

(56) References Cited

OTHER PUBLICATIONS

Bialka et al., "Decontamination of *Escherichia coli* O157:H7 and *Salmonella enterica* on Blueberries Using Ozone and Pulsed UV-Light," Journal of Food Science, 2007, 7 pages, vol. 72, No. 9.
Bialka et al., "Modeling the inactivation of *Escherichia coli* O157:H7 and *Salmonella enterica* on raspberries and strawberries resulting from exposure to ozone or pulsed UV-light," Journal of Food Engineering, 2008, 6 pages, vol. 85.
Bialka et al., "Pulsed UV-light Penetration of Characterization and the Inactivation of *Escherichia coli* K12 in Solid Model Systems," Abstract, American Society of Agricultural and Biological Engineers, 2013, 1 page.
Bialka et al., "Efficacy of Pulsed UV-Light for the Decontamination of *Escherichia coli* O157:H7 and *Salmonella* spp. on Raspberries and Strawberries," Journal of Food Science, 2008, 7 pages, vol. 73, No. 5.
Chang et al., "Removal of Ethylene and Secondary Organic Aerosols Using UV-C 254+185 with TiO2 Catalyst," Aerosol and Air Quality Research, 2013, 9 pages.
Cheba et al., "Inactivation of *E. coli* cell viability and DNA Photo-breakage by Pulsed Nitrogen Laser Radiation," American Institute of Physics, 2005, 5 pages.
Chisari et al., "Improving the quality of fresh-cut melon through inactivation of degradative oxidase and pectinase enzymatic activities by UV-C treatment," Institute of Food Science and Technology, 2011, 6 pages.
Demirci et al., "Disinfection of water by flow-through a Pulsed UV Light Sterilization System," Abstract, Ultrapure Water Journal, 2000, 1 page.
Demirci et al., "Pulsed Ultraviolet Light," Sage Publications, 2008, 5 pages.
Hillegas et al., "Inactivation of Clostridium sporogenes in Clover Honey by Pulsed UV-light Treatment," Abstract, American Society of Agricultural and Biological Engineers, 2013, 1 page.
Jun et al., "Pulsed UV-light treatment of corn meal for inactivation of Aspergillus niger spores," International Journal of Food Science and Technology, 2003, 6 pages.
Kennedy et al., "An investigation of the thermal inactivation of *Staphylococcus aurues* and the potential for increased thermotolerance as a result of chilled storage," Journal of Applied Microbiology, 2005, 7 pages.
Krishnamurthy et al., "Food Processing Operations and Modeling: Design and Analysis," UV Pasteurization of Food Materials, Chapter 11, 2009, 22 pages.
Krishnamurthy et al., "Inactivation of *Staphylococcus aureus* in Milk and Milk Foam by Pulsed UV-Light Treatment and Su+R170rface Response Modeling," Abstract, American Society of Agriculutural and Biological Engineers, 2013, 1 page.
Krishnamurthy et al., "Inactivation of *Staphylococcus aureus* by Pulsed UV-Light Sterilization," Abstract, Journal of Food Protection, 2004, 1 page.
Krishnamurthy et al., "Inactivation of *Staphylococcus aureus* in Milk Using Flow-Through Pulsed UV-Light Treatment System," Journal of Food Science, 2007, 7 pages, vol. 72, No. 7.
Krishnamurthy et al., "Microscopic and Spectroscopic Evaluation of Inactivation of *Staphylococcus aureus* by Pulsed UV Light and Infrared Heating," Food Bioprocess Technology, 2010, 12 pages.
Ozer et al., "Inactivation of *Escherichia coli* O157:H7 and Listeria monocytogenes inoculated on raw salmon fillets by pulsed UV-light treatment," International Journal of Food Science and Technology, 2006, 7 pages.
Sharma et al., "Inactivation of *Escherichia coli* O157:H7 on Inoculated Alfalfa Seed with Pulsed Ultraviolet Light and Response Surface Modeling," Food Microbiology and Safety, 2003, 6 pages.
Zhang et al., "Nonthermal Processing Technologies for Food," Chapters 18 and 19, IFT Press, 2011, 21 pages.
Kim, International Application No. PCT/US2013/057077, Search Report and Written Opinion, dated Nov. 8, 2013, 10 pages.
Yang, International Application No. PCT/US2013/056997, Search Report and Written Opinion, dated Nov. 28, 2013, 12 pages.
Yang, International Application No. PCT/US2013/056986, Search Report and Written Opinion, dated Nov. 29, 2013, 12 pages.
Yang, International Application No. PCT/US2013/056983, Search Report and Written Opinion, dated Dec. 19, 2013, 12 pages.
Cheng, X., Application No. 201380053723.1, Notice of Allowance, dated Mar. 3, 2017, 2 pages (There is no English translation available.).
Cheng, X., Application No. 201380053723.1, Office Action1—English translation, dated Jun. 6, 2016, 11 pages.
Zhou, Z., Application No. 201380056459.7, Office Action1 (with English translation), dated Jun. 14, 2017, 13 pages.
Zhou, Z., Application No. 201380053729.9, Office Action1 (with English translation), dated Mar. 14, 2017, 21 pages.
Li, X., Application No. 201380053801.8, Rejection Decision—with English translation, dated Nov. 6, 2017, 14 pages.
Li, X., Application No. 201380053801.8, Office Action2—with English translation, dated Apr. 21, 2017, 16 pages.
Li, X., Application No. 201380053801.8, Office Action1—English translation, dated Jul. 22, 2016, 7 pages.
Cox, A., U.S. Appl. No. 14/012,637, Notice of Allowance, dated Jan. 19, 2018, 43 pages.
Wang, R., Application No. 201510249047.6, Office Action 1, dated Feb. 11, 2019, 11 pages.
Mayekar, K., U.S. Appl. No. 15/700,533, Notice of Allowance, dated Sep. 21, 2018, 8 pages.
Mendoza-Wilkenfe, E., U.S. Appl. No. 14/012,652, Final Office Action1, dated Sep. 4, 2018, 13 pages.
Mayekar, K., U.S. Appl. No. 15/388,394, Final Office Action, dated Nov. 9, 2018, 7 pages.
Zhou, Z., Application No. 201380053729.9, Rejection Devision (with English translation), dated Jul. 25, 2018, 13 pages.
Martin, E., U.S. Appl. No. 15/670,750, Notice of Allowance, dated Aug. 27, 2018, 7 pages.
Mayekar, K., U.S. Appl. No. 14/012,682, Notice of Allowance 2, dated Apr. 4, 2019, 7 pages.
Martin, E., U.S. Appl. No. 15/982,611, Notice of Allowance, dated Dec. 11, 2018, 11 pages.
Mayekar, K., U.S. Appl. No. 15/388,394, Notice of Allowance, dated May 28, 2019, 7 pages.
Mendoza-Wilkenfe, E., U.S. Appl. No. 14/012,652, Notice of Allowance, dated May 31, 2019, 13 pages.
Mendoza-Wilkenfe, E., U.S. Appl. No. 14/012,652, Office Action1, dated Apr. 9, 2018, 68 pages.
Martin, E., U.S. Appl. No. 15/982,611, Non-Final Rejection, dated Aug. 1, 2018, 31 pages.
Mayekar, K., U.S. Appl. No. 15/388,394, Office Action1, dated Mar. 30, 2018, 81 pages.
Mayekar, K., U.S. Appl. No. 15/700,533, Office Actionl, dated May 22, 2018, 68 pages.
Mendoza-Wilkenfe, E., U.S. Appl. No. 15/941,413, Office Action 1, dated Aug. 20, 2019, 17 pages.
Mayekar, K., U.S. Appl. No. 158/962,574, Office Action 1, dated Sep. 10, 2019, 11 pages.
Cox, Alexis, K., U.S. Appl. No. 15/990,057, Notice of Allowance, dated Oct. 8, 2019, 7 pages.
Application No. 201380053729.9, Notification of Reexamination (with English translation), dated Sep. 24, 2018, received Oct. 10, 2019, 15 pages.

* cited by examiner

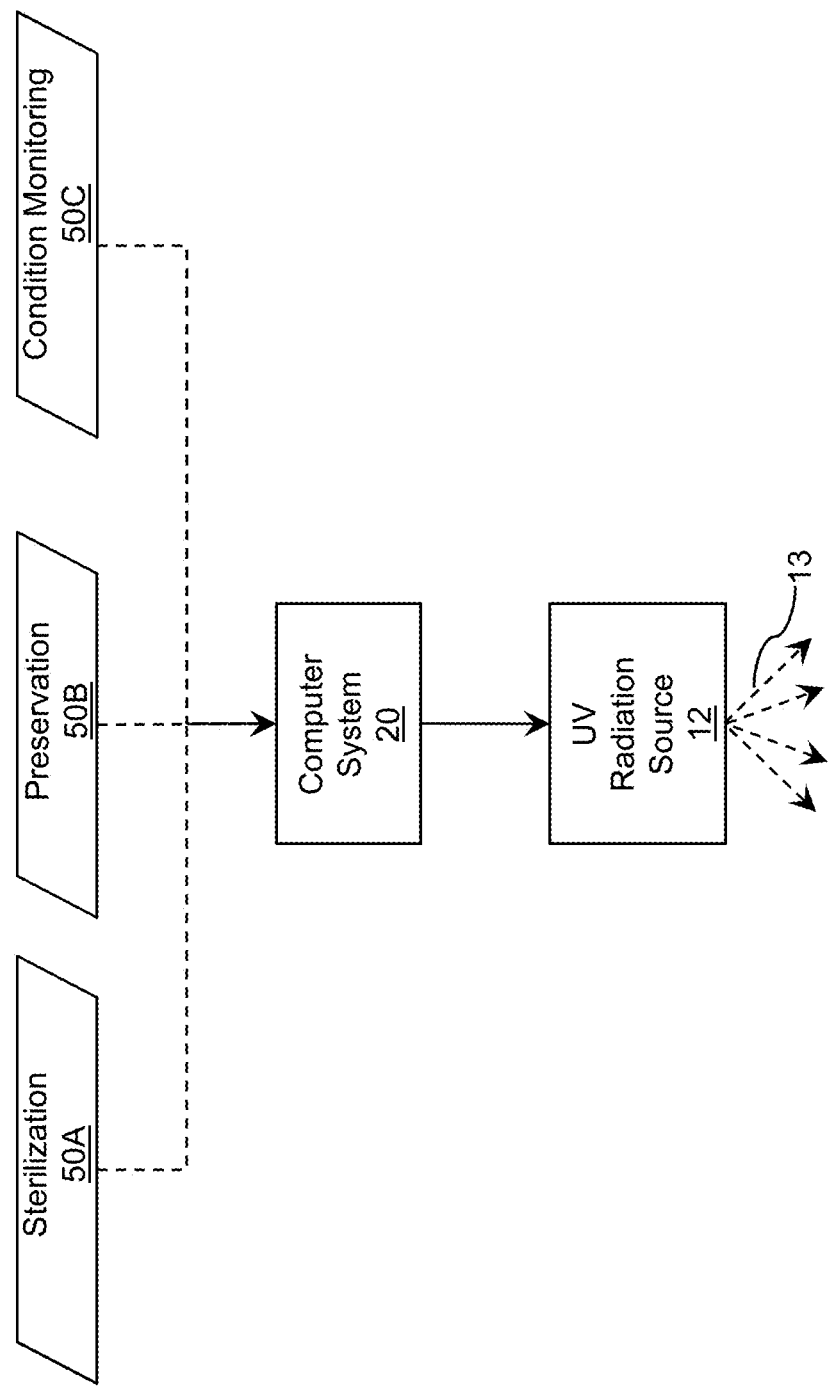

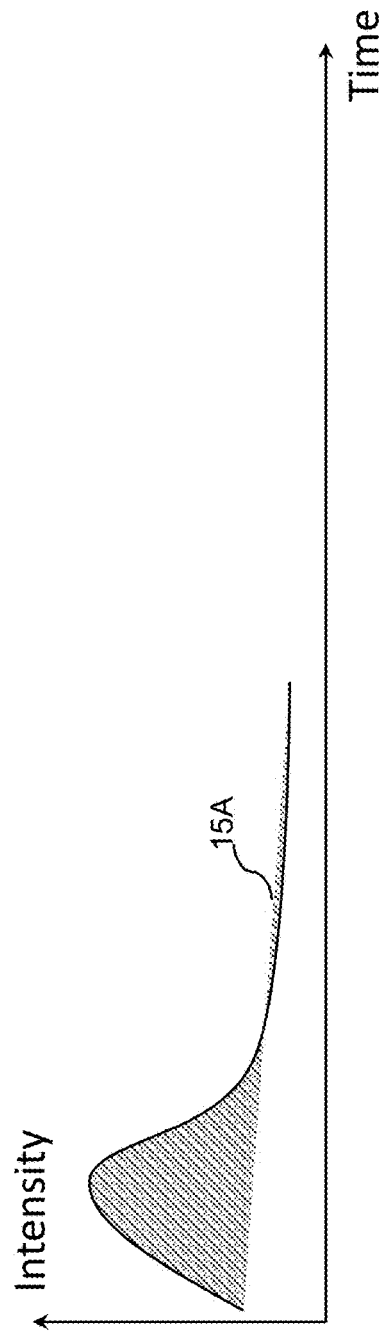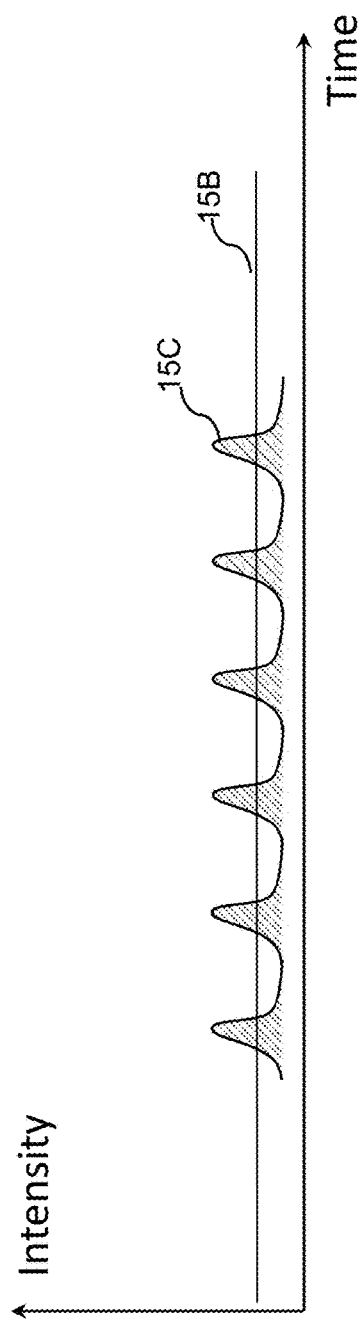

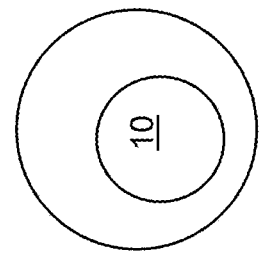
FIG. 8A
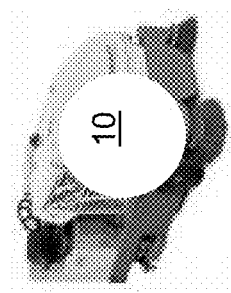
FIG. 8B
FIG. 8C
FIG. 8D
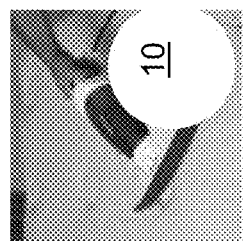
FIG. 8E
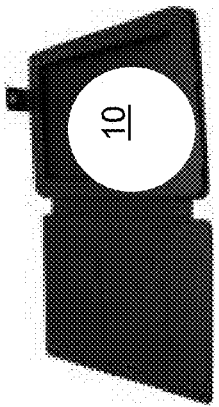

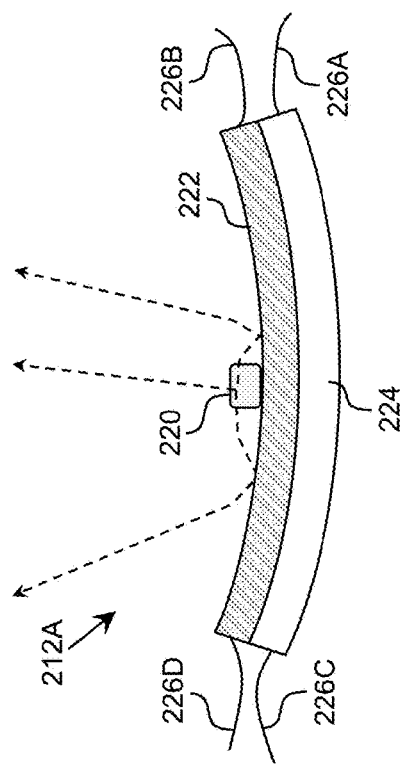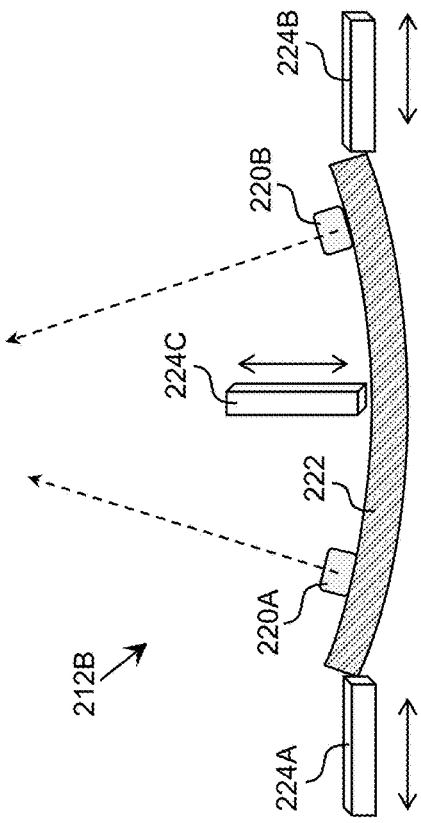

ULTRAVIOLET SYSTEM FOR DISINFECTION

REFERENCE TO RELATED APPLICATION

The current application is a continuation application of U.S. patent application Ser. No. 15/388,506, filed on 22 Dec. 2016, which is a continuation-in-part of U.S. patent application Ser. No. 14/937,090, filed on 10 Nov. 2015, which is a continuation-in-part of U.S. patent application Ser. No. 14/012,644, filed on 28 Aug. 2013, which claims the benefit of U.S. Provisional Application No. 61/694,236, filed on 28 Aug. 2012, all of which are hereby incorporated by reference.

TECHNICAL FIELD

The disclosure relates generally to ultraviolet radiation, and more particularly, to a solution for sterilizing, preserving, and/or the like, a storage area of a storage device using ultraviolet radiation.

BACKGROUND ART

Reliable, hygienic storage of sanitary and biological items, such as food, is a major problem. For example, the problem is present throughout the food industry, e.g., manufacturers, retailers, restaurants, and in every household, and is especially significant for food service establishments, in which related issues of food quality control also are significant. In addition to food storage and quality control in fixed locations (e.g., a refrigerator) where access to electricity is readily available, proper food storage and quality control also is important in situations for which access to unlimited electricity and/or a stationary storage device, such as a refrigerator, is not available, such as picnics, camping, mobile food kiosks, hospitality or battlefield meal locations, search and rescue, etc. In addition to food, other stored items also require hygienic storage. For example, medical and chemical equipment, construction wood, etc., also require storage in a biologically safe environment. Since ambient temperature significantly affects bacterial activity, effective control of the ambient temperature is an important tool in ensuring reliable, hygienic storage of various items.

Fresh food products can be processed using ultraviolet light as a germicidal medium to reduce the food-born microbial load. Water has been treated with ultraviolet light to provide safe drinking water for quite some time. Fruit and vegetable products capable of being pumped through a system generally are very suitable for processing by ultraviolet light to reduce the microbial load. Today, most of these products are pasteurized to obtain microbiologically safe and nutritious products. However, pasteurization can change the taste and flavor of such products because of the temperature and processing time. Juices from different sources can be treated by exposure to ultraviolet light at different doses. On the other hand, variables such as exposure time, type of fruit product, juice color and juice composition, among other variables, need to be studied to obtain fruit products with reduced microbial load, increased shelf life and adequate sensory and nutritional characteristics. Reduction of microbial load through ultraviolet light application as a disinfection medium for food products other than liquids also is being studied. Moreover, ultraviolet technology could be a source for pasteurization of liquids, or disinfection of solid foods as an alternative technology, instead of thermal treatment or application of antimicrobial compounds.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/$cm^2$ is adequate to deactivate approximately 99 percent of the pathogens.

Various approaches have sought to use ultraviolet light to disinfect a compartment, such as compartments found in refrigerators. For example, one approach proposes a plurality of small, low current UV lights which utilize the standard circuitry of the refrigerator to power the UV light source. Another approach uses a UV lamp installed in a top portion of the refrigerator and reflective lining throughout the interior to reflect the UV radiation throughout the compartment. Another approach provides a UV system with a single UV source attached to an internal sidewall of a refrigerator to radiate light to the entire compartment, or in the alternative, provide UV exposure to a limited compartment. Still another approach proposes an air cleaner for an internal compartment of a refrigerator, which utilizes a UV filter to reduce pathogens in the re-circulated air. Still another approach provides a refrigerator with UV light irradiation components to eradicate low-level light from the storage containers contained therein to promote freshness of foodstuffs.

SUMMARY OF THE INVENTION

The inventors provide a solution for the sterilization, preservation, disinfection, decontamination, and/or the like, of a storage area of a storage device using ultraviolet radiation. For example, an embodiment of the solution is configured to appropriately apply a target intensity and/or wavelength of ultraviolet radiation to preserve, sterilize, disinfect, decontaminate, and/or the like, the storage area by destroying and/or suppressing the reproductive function of viruses and/or bacteria, which may be located within the storage area. Similarly, this solution may be implemented as part of other storage environments, such as pantries, grocery bags, boxes, biological object storage containers, and/or the like.

Aspects of the invention provide a solution in which ultraviolet radiation is directed within an area. The target wavelength ranges and target intensity ranges of the ultraviolet radiation sources can correspond to at least one of a plurality of selectable operating configurations including a sterilization operating configuration, and a preservation operating configuration.

A first aspect of the invention provides a system comprising: at least one ultraviolet radiation source configured to generate ultraviolet radiation directed within a storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using at least one of a plurality of selectable operating configurations and the set of current conditions, the selectable operating configurations including: a sterilization operating configuration, and a preservation operating configuration.

A second aspect of the invention provides a food storage device comprising: a storage area configured to store at least one perishable food item; at least one ultraviolet radiation source configured to generate ultraviolet radiation directed within the storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using at least one of a plurality of selectable operating configurations and the set of current conditions, the selectable operating configurations including: a sterilization operating configuration, and a preservation operating configuration.

A third aspect of the invention provides a refrigeration device comprising: a storage area configured to store at least one refrigerated item; a component configured to control at least one environmental condition of the storage area, wherein the at least one environmental condition includes at least one of: a temperature, a humidity, a gas convection, or a fluid convection; at least one ultraviolet radiation source configured to generate ultraviolet radiation directed within the storage area; and a monitoring and control system for managing the storage area by performing a method comprising: monitoring a set of current conditions of at least one of: the storage area or a set of items located in the storage area; and controlling ultraviolet radiation generated by the at least one ultraviolet radiation source using at least one of a plurality of selectable operating configurations and the set of current conditions, the selectable operating configurations including: a sterilization operating configuration, and a preservation operating configuration.

A fourth aspect of the invention provides a system comprising: at least one ultraviolet radiation source configured to generate ultraviolet radiation directed within a storage area; and a monitoring and control system configured to: monitor a set of current conditions of at least one of: the storage area or a set of items located in the storage area; and control ultraviolet radiation generated by the at least one ultraviolet radiation source using at least one of a plurality of selectable operating configurations and the set of current conditions, the selectable operating configurations including: a sterilization operating configuration, a preservation operating configuration, and a condition monitoring operating configuration, wherein the sterilization operating configuration is configured to disinfect the storage area, the preservation operating configuration is configured to provide a particular level of repression for microorganism growth, and the condition monitoring operating configuration is configured to detect microorganisms within the storage area, wherein the controlling includes adjusting at least one of: a location within the storage area to which the ultraviolet radiation is directed, a direction of the ultraviolet radiation emitted by the at least one ultraviolet radiation source, or a time scheduling of the ultraviolet radiation emitted by the at least one ultraviolet radiation source.

A fifth aspect of the invention provides a food storage device comprising: a storage area configured to store at least one perishable food item; at least one ultraviolet radiation source configured to generate ultraviolet radiation directed within the storage area; and a monitoring and control system configured to: monitor a set of current conditions of at least one of: the storage area or a set of items located in the storage area; and control ultraviolet radiation generated by the at least one ultraviolet radiation source using at least one of a plurality of selectable operating configurations and the set of current conditions, the selectable operating configurations including: a sterilization operating configuration, a preservation operating configuration, and a condition monitoring operating configuration, wherein the sterilization operating configuration is configured to disinfect the storage area, the preservation operating configuration is configured to provide a particular level of repression for microorganism growth, and the condition monitoring operating configuration is configured to detect microorganisms within the storage area, wherein the controlling includes adjusting at least one of: a location within the storage area to which the ultraviolet radiation is directed, a direction of the ultraviolet radiation emitted by the at least one ultraviolet radiation source, or a time scheduling of the ultraviolet radiation emitted by the at least one ultraviolet radiation source.

A sixth aspect of the invention provides a refrigeration device comprising: a storage area configured to store at least one refrigerated item; a component configured to control at least one environmental condition of the storage area, wherein the at least one environmental condition includes at least one of: a temperature, a humidity, a gas convection, or a fluid convection; at least one ultraviolet radiation source configured to generate ultraviolet radiation directed within the storage area; and a monitoring and control system configured to: monitor a set of current conditions of at least one of: the storage area or a set of items located in the storage area; and control ultraviolet radiation generated by the at least one ultraviolet radiation source using at least one of a plurality of selectable operating configurations and the set of current conditions, the selectable operating configurations including: a sterilization operating configuration, a preservation operating configuration, and a condition monitoring operating configuration, wherein the sterilization operating configuration is configured to disinfect the storage area, the preservation operating configuration is configured to provide a particular level of repression for microorganism growth, and the condition monitoring operating configuration is configured to detect microorganisms within the storage area, wherein the controlling includes adjusting at least one of: a location within the storage area to which the ultraviolet radiation is directed, a direction of the ultraviolet radiation emitted by the at least one ultraviolet radiation source, or a time scheduling of the ultraviolet radiation emitted by the at least one ultraviolet radiation source.

A seventh aspect of the invention provides a system comprising: a set of ultraviolet radiation sources configured to generate ultraviolet radiation directed within a storage area; and an external interface configured to receive an input from a user; a feedback component including at least one camera configured to monitor a set of current conditions of at least one of: the storage area or a set of items located in the storage area; and a control system configured to control the ultraviolet radiation generated by the set of ultraviolet radiation sources using at least one of: the set of current conditions monitored by the feedback component and the input from the user, wherein the controlling includes adjusting at least one of: a location within the storage area to which the ultraviolet radiation is directed, a direction of the ultraviolet radiation, or a time scheduling of the ultraviolet radiation, a radiation wavelength of the ultraviolet radiation, an intensity of the ultraviolet radiation, or a pattern of the ultraviolet radiation.

An eighth aspect of the invention provides a food storage device comprising: a storage area configured to store a set of items; a set of ultraviolet radiation sources configured to generate ultraviolet radiation directed within the storage area; an external interface configured to receive an input from a user; a feedback component including at least one camera configured to monitor a set of current conditions of at least one of: the storage area or a set of items located in the storage area; and a control system configured to control the ultraviolet radiation generated by the set of ultraviolet radiation sources using at least one of: the set of current conditions monitored by the feedback component and the input from the user, wherein the controlling includes adjusting at least one of: a location within the storage area to which the ultraviolet radiation is directed, a direction of the ultraviolet radiation, a time scheduling of the ultraviolet radiation, a radiation wavelength of the ultraviolet radiation, an intensity of the ultraviolet radiation, or a pattern of the ultraviolet radiation.

A ninth aspect of the invention provides a refrigeration device comprising: a storage area configured to store at least one refrigerated item; a component configured to control at least one environmental condition of the storage area, wherein the at least one environmental condition includes at least one of: a temperature, a humidity, a gas convection, or a fluid convection; a set of ultraviolet radiation sources configured to generate ultraviolet radiation directed within the storage area; an external interface configured to receive an input from a user; a feedback component including at least one camera configured to monitor a set of current conditions of at least one of: the storage area or a set of items located in the storage area; and a control system configured to control the ultraviolet radiation generated by the set of ultraviolet radiation sources using at least one of: the set of current conditions monitored by the feedback component and the input from the user, wherein the controlling includes adjusting at least one of: a location within the storage area to which the ultraviolet radiation is directed, a direction of the ultraviolet radiation, a time scheduling of the ultraviolet radiation, a radiation wavelength of the ultraviolet radiation, an intensity of the ultraviolet radiation, or a pattern of the ultraviolet radiation.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 2 shows a block diagram illustrating use of operating configurations for operating an ultraviolet radiation source according to an embodiment.

FIGS. 3A-3B show graphs of illustrative intensity levels of ultraviolet radiation for operating configurations for operating an ultraviolet radiation source according to an embodiment.

FIGS. 8A-8E show illustrative storage devices for use with an ultraviolet radiation system according to embodiments.

FIGS. 11A-11B show illustrative ultraviolet radiation sources according to additional embodiments.

FIG. 13A shows an illustrative storage device according to an embodiment, while

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution in which ultraviolet radiation is directed within an area. The target wavelength ranges and/or target intensity ranges of the ultraviolet radiation sources can correspond to at least one of a plurality of selectable operating configurations including a sterilization operating configuration, and a preservation operating configuration. As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As also used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through. In an embodiment, the ultraviolet transparent structure is formed of a material and has a thickness, which allows at least ten percent of the ultraviolet radiation to pass there through.

Figure 1:
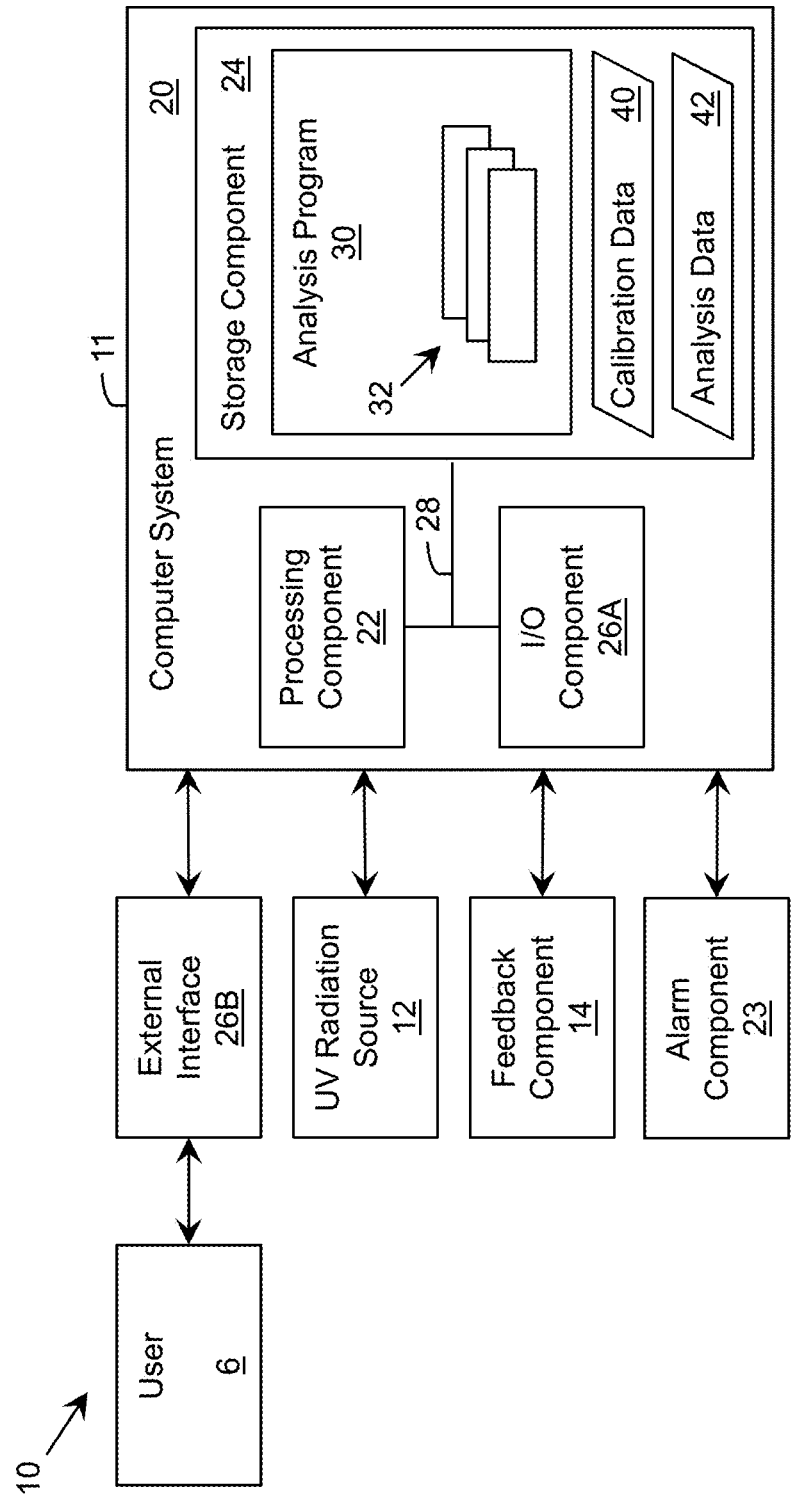
FIG. 1 shows an illustrative ultraviolet radiation system according to an embodiment.

Turning to the drawings, FIG. 1 shows an illustrative ultraviolet radiation system 10 according to an embodiment. In this case, the system 10 includes a monitoring and/or control system 11, which is implemented as a computer system 20 including an analysis program 30, which makes the computer system 20 operable to manage an ultraviolet (UV) radiation source 12 by performing a process described herein. In particular, the analysis program 30 can enable the computer system 20 to operate the UV radiation source 12 to generate and direct ultraviolet radiation within an area and process data corresponding to one or more conditions of the area and/or an item located in the area, which is acquired by a feedback component 14. While a single UV radiation source 12 is shown, it is understood that the area can include any number of UV radiation sources 12, the operation of which the computer system 20 can separately manage using a process described herein.

In an embodiment, during an initial period of operation (e.g., after recent access to the area, addition/removal/reconfiguration of item(s) placed within the area, and/or the like), the computer system 20 can acquire data from the feedback component 14 regarding one or more attributes of the items in the area and/or conditions of the area and generate analysis data 42 for further processing. The analysis data 42 can include information on the color, appearance, and/or the like, of items in the area, the presence of microorganisms on the items or within the area, and/or the like. Furthermore, the analysis data 42 can include information on the presence of ethylene gas within the area. The computer system 20 can use the analysis data 42 to generate calibration data 40 for controlling one or more aspects of the ultraviolet radiation generated by the ultraviolet radiation source(s) 12 using one of a plurality of selectable operating configurations as discussed herein. Furthermore, one or more aspects of the operation of the ultraviolet radiation source 12 can be controlled by a user 6 via an external interface component 26B.

The computer system 20 is shown including a processing component 22 (e.g., one or more processors), a storage component 24 (e.g., a storage hierarchy), an input/output (I/O) component 26A (e.g., one or more I/O interfaces and/or devices), and a communications pathway 28. In general, the processing component 22 executes program code, such as the analysis program 30, which is at least partially fixed in the storage component 24. While executing program code, the processing component 22 can process data, which can result in reading and/or writing transformed data from/to the storage component 24 and/or the I/O component 26A for further processing. The pathway 28 provides a communications link between each of the components in the computer system 20. The I/O component 26A and/or the external interface component 26B can comprise one or more human I/O devices, which enable a human user 6 to interact with the computer system 20 and/or one or more communications devices to enable a system user 6 to communicate with the computer system 20 using any type of communications link. To this extent, during execution by the computer system 20, the analysis program 30 can manage a set of interfaces (e.g., graphical user interface(s), application program interface, and/or the like) that enable human and/or system users 6 to interact with the analysis program 30.

Furthermore, the analysis program 30 can manage (e.g., store, retrieve, create, manipulate, organize, present, etc.) the data, such as calibration data 40 and analysis data 42, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent monitoring and/or control systems 11 that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 11 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 20. However, it is understood that the functionality described in conjunction therewith can be implemented by any type of monitoring and/or control system 11.

Regardless, when the computer system 20 includes multiple computing devices, the computing devices can communicate over any type of communications link. Furthermore, while performing a process described herein, the computer system 20 can communicate with one or more other computer systems, such as the user 6, using any type of communications link. In either case, the communications link can comprise any combination of various types of wired and/or wireless links; comprise any combination of one or more types of networks; and/or utilize any combination of various types of transmission techniques and protocols. This communications link, which can include a wireless or cable based transmission, can be utilized to transmit information about the state of one or more items and/or zones within the storage area 54.

The system 10 can be implemented within an existing storage device (e.g., a refrigerator) using any solution. For example, one or more ultraviolet radiation sources 12 and one or more devices included in a feedback component 14 can be fixed within various locations in the storage device (e.g., on walls, shelves, etc.) and configured for operation by the computer system 20. The locations of devices in the ultraviolet radiation source(s) 12 and/or the feedback component 14 can be selected to provide comprehensive coverage of the storage area of the storage device and the items located within the storage area. In an embodiment, the computer system 20 can be located outside of the storage area of the storage device.

The ultraviolet radiation source 12 can comprise any combination of one or more ultraviolet radiation emitters. For example, the UV source 12 can include a high intensity ultraviolet lamp (e.g., a high intensity mercury lamp), an ultraviolet light emitting diode (LED), and/or the like. In an embodiment, the UV source 12 includes a set of light emitting diodes manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). Additionally, the UV source 12 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, within the storage area. Illustrative wave guiding structures include, but are not limited to, a plurality of ultraviolet fibers, each of which terminates at an opening, a diffuser, and/or the like. The computer system 20 can independently control each UV source 12.

The system 10 also can include an alarm component 23, which can be operated by the computer system 20 to indicate when ultraviolet radiation is being directed within the storage area. The alarm component 23 can include one or more devices for generating a visual signal, an auditory signal, and/or the like. For example, in the example shown in FIG. 5A, where the storage device 52 includes a refrigeration device, a panel 8 can display a flashing light, text, an image, and/or the like, to indicate that ultraviolet radiation is currently being directed into a corresponding storage area 54. Furthermore, the alarm component 23 can generate a noise, such as a bell, a beep, and/or the like, to indicate that ultraviolet radiation is currently being directed to the storage area 54.

FIG. 2 shows a block diagram illustrating use of operating configurations for operating an ultraviolet radiation source 12 according to an embodiment. As illustrated, the computer system 20 can use data corresponding to a selected operating configuration 50A-50C to adjust one or more aspects of the ultraviolet radiation 13 generated by the ultraviolet radiation source(s) 12. In an embodiment, the operating configurations 50A-50C include a sterilization operating configuration 50A, a preservation operating configuration 50B, and a condition monitoring operating configuration 50C. In an embodiment, the sterilization operating configuration 50A is configured to disinfect, sterilize, and/or eradicate the storage area of microorganisms. The sterilization operating configuration 50A also can be configured to perform chemical decontamination using any solution. The preservation operating configuration 50B is configured to prevent dark reactivation and photoreactivation of microorganisms to avoid microorganism growth above acceptable levels, as discussed herein. Additionally, the computer system 20 can operate the ultraviolet radiation source 12 in a condition monitoring operating configuration 50C, during which a relatively low level of ultraviolet radiation can be generated in order to detect bacteria and/or the like, which may fluoresce in the ultraviolet light. The condition monitoring operating configuration 50C can be utilized to identify the need for sterilization and/or evaluate an effectiveness of sterilization previously performed.

The computer system 20 is configured to control and adjust a direction, an intensity, a pattern, and/or a spectral power (e.g., wavelength) of the UV sources 12 to correspond to a particular operating configuration 50A-50C. The computer system 20 can control and adjust each property of the UV source 12 independently. For example, the computer system 20 can adjust the intensity, the time duration, and/or time scheduling (e.g., pattern) of the UV source 12 for a given wavelength. Each operating configuration 50A-50C can designate a unique combination of: a target ultraviolet wavelength, a target intensity level, a target pattern for the ultraviolet radiation (e.g., time scheduling, including duration (e.g., exposure/illumination time), duty cycle, time between exposures/illuminations, and/or the like), a target spectral power, and/or the like, in order to meet a unique set of goals corresponding to each operating configuration 50A-50C.

For the sterilization operating configuration 50A, a target wavelength range can be approximately 250 nanometers to approximately 310 nanometers. Referring to FIG. 3A, a graph illustrating the intensity level 15A for the ultraviolet radiation over time (both in arbitrary units) of the sterilization operating configuration 50A is shown. The intensity level 15A can be a high intensity short burst of ultraviolet radiation. In an embodiment, the intensity level and time are selected to provide a dose sufficient to achieve a 6 log inactivation of bacteria. For example, such a dose can range between approximately 10 and approximately 100 milli-Joules/$cm^2$. In this case, the intensity of the ultraviolet radiation can be selected to provide an overall exposure integrated over the period of exposure to provide such a dose. An illustrative period of exposure comprises a few microseconds. Regardless, it is understood that this level of inactivation is only illustrative and other levels of inactivation can be selected. For the preservation operating configuration 50B, a target wavelength range can be approximately 190 nanometers to approximately 285 nanometers. Referring to FIG. 3B, a graph illustrating the intensity level for the ultraviolet radiation over time (both in arbitrary units) of the preservation operating configuration 50B is shown. The intensity level can be a low intensity ultraviolet radiation that can be either continuous 15B or periodic 15C. The intensity level also can be aperiodic at a predetermined schedule. For the periodic/aperiodic intensity level 15C, the intensity level/duration and period (e.g., time between peaks) can be chosen to be commensurable with the preservation operating configuration 50B, such that microorganisms present in the storage area are prevented from growing upon a predetermined level. Regardless, it is understood that a selected intensity and duration for either operating condition can be adjusted based on one or more of: a target microorganism, a desired level of suppression/inactivation, a wavelength of the ultraviolet radiation, and/or the like.

Figure 4:
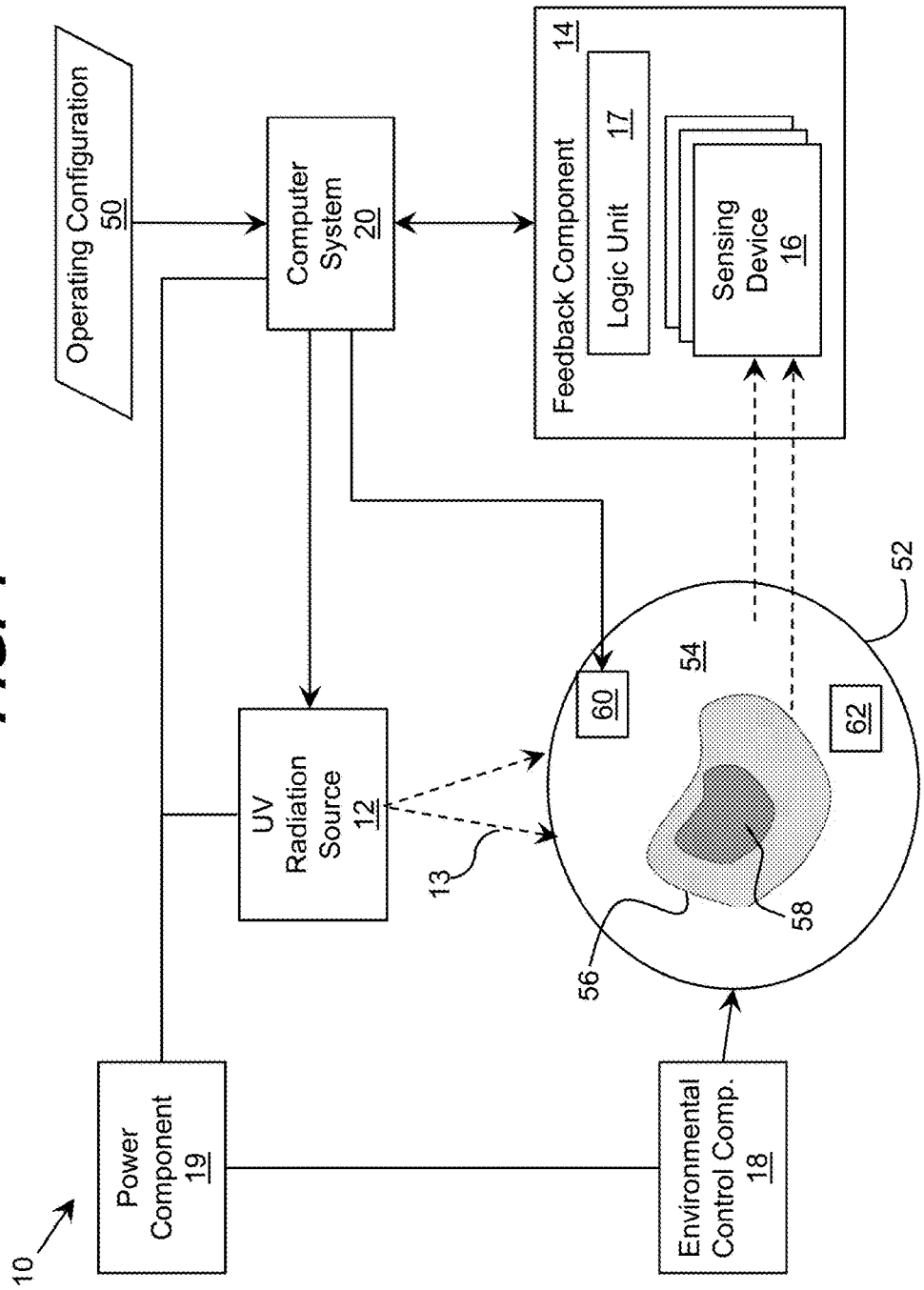
FIG. 4 shows an illustrative system including an ultraviolet radiation system according to an embodiment.

FIG. 4 shows an illustrative system including an ultraviolet radiation system 10 according to an embodiment. The computer system 20 is configured to control the UV source 12 to direct ultraviolet radiation 13 into a storage area 54 of a storage device 52, within which a set of items 56 are located. The feedback component 14 is configured to acquire data used to monitor a set of current conditions of the storage area 54 and/or the items 56 over a period of time. As illustrated, the feedback component 14 can include a plurality of sensing devices 16, each of which can acquire data used by the computer system 20 to monitor the set of current conditions.

It is understood that the set of current conditions in the storage area 54 can include one or more attributes corresponding to a set of biological activity dynamics present within the storage area. The set of biological activity dynamics can include, for example, a presence of biological activity (e.g., exponential bacterial growth), a location of the biological activity, a type of biological activity (e.g., type of organism), a concentration of the biological activity, an estimated amount of time an organism has been in a growth phase (e.g., exponential growth and/or stationary), and/or the like. The set of biological activity dynamics can include information on the variation of the biological activity over time, such as a growth rate, a rate with which an area including the biological activity is spreading, and/or the like. In an embodiment, the set of biological activity dynamics are related to various attributes of bacteria and/or virus activity within an area, including, for example, the presence of detectable bacteria and/or virus activity, measured bacteria and/or virus population/concentration time dynamics, growth phase, and/or the like.

In an embodiment, the sensing devices 16 include at least one of a visual camera or a chemical sensor. The visual camera can acquire data (e.g., visual, electronic, and/or the like) used to monitor the storage area 54 and/or one or more of the items 56 located therein, while the chemical sensor can acquire data (e.g., chemical, electronic, and/or the like) used to monitor the storage area 54 and/or one or more of the items 56 located therein. The set of current conditions of the storage area 54 and/or items 56 can include the color or visual appearance of the items 56, the presence of microorganisms within the storage area 54, and/or the like. For example, when the computer system 20 is operating the UV radiation source 12, a visual camera and/or a chemical sensor monitoring the storage area 54 may be operated to detect the presence of microorganisms. In a specific embodiment, the visual camera comprises a fluorescent optical camera that can detect bacteria 56 and/or viruses 58 that become fluorescent under ultraviolet radiation.

Furthermore, the computer system 20 can process image data acquired by a visual camera to evaluate one or more aspects of a surface of an article, such as a food item, and determine a treatment required. During such processing, the computer system 20 can detect a region of a surface that is discolored, includes mold, and/or the like. The computer system 20 can identify such discoloration by analyzing a change in color measured over a period of time in which the article has been imaged. Similarly, the computer system 20 can process image data acquired by an infrared camera to detect a change in surface temperature, e.g., due to the presence of mold or discoloration, and determine a treatment required based on the change.

However, it is understood that a visual camera and a chemical sensor are only illustrative of various types of sensors that can be implemented. For example, the sensing devices 16 can include one or more mechanical sensors (including piezoelectric sensors, various membranes, cantilevers, a micro-electromechanical sensor or MEMS, a nanomechanical sensor, and/or the like), which can be configured to acquire any of various types of data regarding the storage area 54 and/or items 56 located therein. In another embodiment, the sensing devices 16 can include a UV detector that is configured to detect ultraviolet radiation within the storage area 54. The absorption of ultraviolet radiation within storage area 54 can indicate the presence of bacteria 56 and/or virus 58. The UV detector can be a solid state ultraviolet radiation detector manufactured with one or more layers of materials selected from the group-III nitride material system (e.g., $Al_XIn_YGa_{1-X-Y}N$, where $0 \le X$, $Y \le 1$, and $X+Y \le 1$ and/or alloys thereof). For example, the UV detector can comprise any type of ultraviolet sensing device, such as an ultraviolet-sensitive photodetector (e.g., an ultraviolet photodiode). In an embodiment, the UV detector can be selected based on its sensitivity to a particular, narrow band of ultraviolet light, which can be selected using any solution. Additionally, the UV detector can comprise one or more additional components (e.g., a wave guiding structure, filter, system for moving and/or redirecting ultraviolet detector(s), etc.) to detect ultraviolet radiation in a particular location/direction, and make the UV detector sensitive to a particular range of wavelengths, and/or the like.

The feedback component 14 also can include one or more additional devices. For example, the feedback component 14 is shown including a logic unit 17. In an embodiment, the logic unit 17 receives data from a set of sensing devices 16 and provides data corresponding to the set of conditions of the storage area 54 and/or items 56 located in the storage area 54 for processing by the computer system 20. In a more particular embodiment, the computer system 20 can provide information corresponding to the currently selected operating configuration 50 for use by the feedback component 14. For example, the logic unit 17 can adjust the operation of one or more of the sensing devices 16, operate a unique subset of the sensing devices 16, and/or the like, according to the currently selected operating configuration 50. In response to data received from the feedback component 14, the computer system 20 can automatically adjust and control one or more aspects of the ultraviolet radiation 13 generated by the ultraviolet radiation source 12 according to the currently selected operating configuration 50.

Figure 13C:
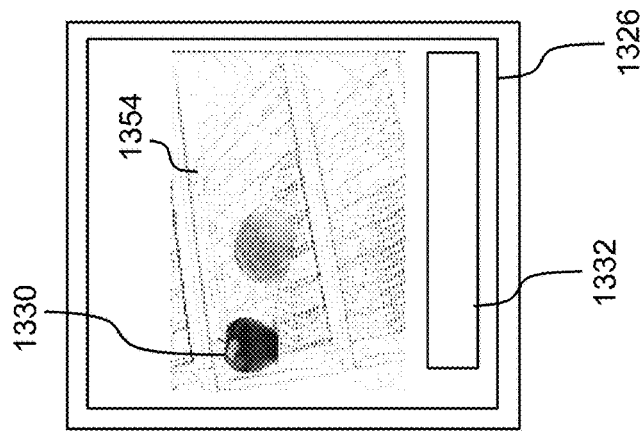
FIGS. 13B-13C show illustrative interfaces according to embodiments.
Figure 13B:
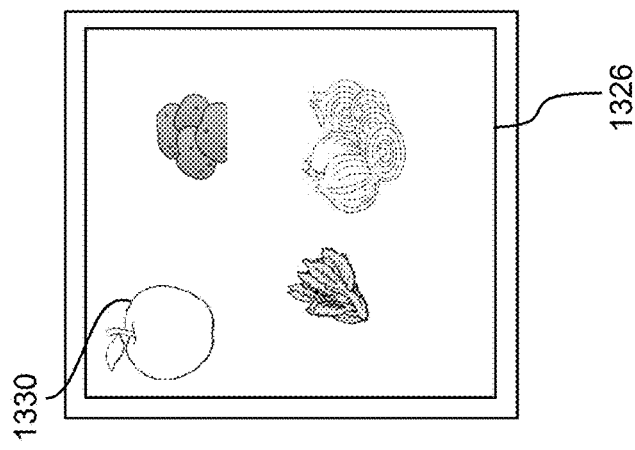
Figure 13A:
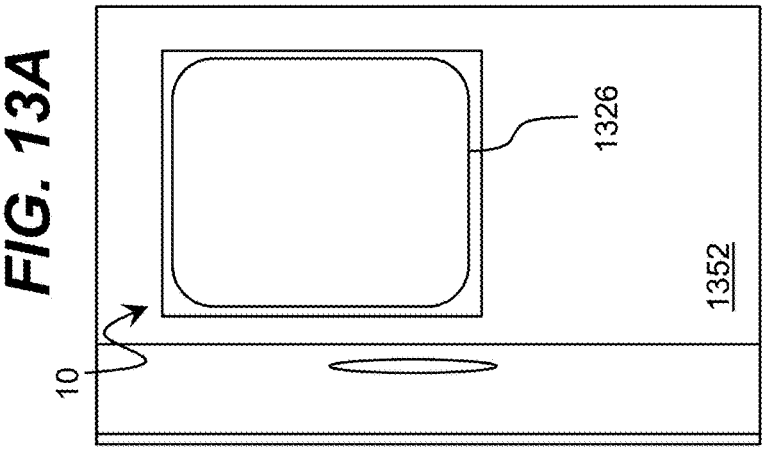

In an embodiment, the visual camera can be used to provide a visual representation and/or information regarding the storage area 54 and/or items within the storage area 54 to a user 6 (FIG. 1) via an interface located on the storage device 52 (e.g., an external interface 26B). For example, turning to FIGS. 13A-13C, an illustrative storage device 1352 (e.g., a refrigerator) with an interface 1326 according to an embodiment is shown in FIG. 13A, while illustrative interfaces 1326 are shown in FIGS. 13B and 13C. An interface 1326 can include a touchscreen that allows a user to control the system 10 using the interface 1326. In an embodiment, the user can use the interface 1326 to adjust any of the components of the system 10 (FIG. 4). For example, the user can use the interface 1326 to adjust the settings on the ultraviolet radiation source 12. The system 10 can include a feedback component 14 (FIG. 4) that includes a visual camera and a light source (e.g., a light emitting diode (LED)) to provide a visual representation of the item(s) within the storage area 1354 of the storage device 1352 on the interface 1326. The interface 1326 can display a real-time visual representation of the items or different sections within the storage area 1354 using the visual camera and the light source. For example, in FIG. 13C, an illustrative real-time visual representation of the storage area 1354 is shown on an interface 1326 according to an embodiment. The interface 1326 in FIG. 13C shows the food items 1330 within the storage area 1354. The interface 1326 can include a menu 1332 that allows a user to search for a particular item within the storage device 1352. In an embodiment, the user can use the menu 1332 to log data regarding an item 1330 within the storage device 1352. For example, the user can touch an area of the interface 1326 corresponding to a particular item and use the menu 1332 to indicate what the item is. For example, the user can type the name of the item in the menu 1332 and the computer system 20 (FIG. 4) can search in a database for that item name. In another embodiment, the user can select the name of the item from a list displayed on the menu 1332. The menu 1332 can also display an option to zoom in on a particular item 1330 located within the storage area 1354.

Turning now to FIG. 13B, the interface 1326 can also display a graphical representation of all the items 1330 located within the storage area 1354 and data regarding each of the items 1330. For example, the data regarding each of the items 1330 can include: the name of the item 1330, the location of the item 1330 within the storage area 1354, the UV radiation treatment for the item 1330, the status of the item 1330 (e.g., whether the item 1330 will spoil soon, a predicted schedule of lifetime for the item 1330), and/or the like. With regard to the UV radiation treatment for the item 1330, the interface 1326 can indicate what type of UV radiation treatment can be used to treat the particular item 1330. For example, if the item is a produce item, such as strawberries, UV-A, UV-B, and/or UV-C radiation can be used to prolong storage life through the generation of antioxidants as well as disinfect the item surface and eliminate the growth of mold or bacteria. In another embodiment, if the item is a meat item, UV-C radiation is generally used for surface disinfection. In an embodiment, the storage device 1352 can have preferred locations for different food items due to a particular arrangement of UV-A, UV-B, UV-C sources located within the storage area 1354. The interface 1326 can display other data such as: a frequency of access to each section in the storage area 1354, a warning for items that will spoil soon, a list of recipes for the items stored in the storage area 1354, a notification for automatically ordering items when the quality and/or quantity of the item is below a target threshold, and/or the like.

In operation, the feedback component 14 (FIG. 4) that includes a visual camera and light source can be used to monitor the growth of microorganisms on the surface of items 1330 within the storage area 1354 in order to determine (e.g., using logic unit 17) what radiation (UV-A, UV-B, UV-C, visible, blue, and/or the like) combined with the addition or removal of humidity (e.g., via environmental control component 18) and/or ethylene (e.g., via chamber 60) is required to disinfect and control the growth on microorganisms on the surface of the items 1330. In an embodiment, the storage area 1354 can include a set of non-interacting compartments, where the ambient characteristics of each compartment are controlled separately. The ambient characteristics include control of the humidity levels, the ethylene levels, the ultraviolet radiation levels, and/or the like. The visual camera and light source can be used to determine the type of items 1330 located within the storage area 1354 and adjust at least one of: the wavelength, dose, spatial pattern, intensity, time dependence, or any combination for the ultraviolet radiation source 12. In an embodiment, the optimum radiation parameters for the items 1330 can be determined by a preprogrammed database stored in the computer system 12. In another embodiment, the optimum radiation parameters for the items 1330 can be determined by a fluorescent spatial and spectral patterns observed by the visual camera and light source (e.g., delivering ultraviolet radiation to the items and storage area 1354 and detecting the fluorescent signal (spatial and spectral pattern) from the storage area 1354 and items 1330). The data from the feedback component 14 can be displayed on the interface 1326 for the user. The user can use the interface 1326 to control and adjust the parameters of the ultraviolet radiation emitted by the ultraviolet radiation source 12 (FIG. 4). The control and adjustment of the parameters can be based on user preferences, residence time of an item 1330 within the storage area 1354, and/or the like. In an embodiment, an alarm component 23 (FIG. 1) can alarm a user regarding the declining state of an item 1330.

In an embodiment, a form and shape of the storage device 1352 can be different from a typical refrigerator. For example, regions of the storage device 1352 can be difficult to access by a user and include mechanisms to deliver the items 1330 within the area to the user. For example, the storage device 1352 can include a moving drawer. A request by the user for an item 1330 to be delivered can be inputted through the interface 1326. Furthermore, the storage area 1354 can be divided into several areas, such as shelves (e.g., shelf 72 in FIG. 9 and shelves shown in FIG. 13C). The ultraviolet radiation in each area can be separately controlled by the computer system 20 (FIG. 4).

For any of the embodiments of a storage device discussed herein, the computer system 20 (FIG. 1) is capable of upgrading the firmware through any type of connection. In an embodiment, the firmware is upgraded using an internet connection.

For any of the embodiments of a storage device discussed herein, the functionality of the ultraviolet radiation system 10 can be controlled from any distance. As mentioned above, the I/O component 26A (FIG. 1) and/or the external interface component 26B can comprise one or more human I/O devices, which enable a human user 6 to interact with the computer system 20 and/or one or more communications devices to enable a system user 6 to communicate with the computer system 20 using any type of communications link. In an embodiment, the computer system 20 can be controlled by a user on a mobile device (e.g., laptop, smartphone, tablet, and/or the like) using a wired or wireless communications link. The user can use the mobile device (e.g., an app installed and executing thereon) to modify the UV radiation, obtain a status on the items within the storage area, and/or the like. For example, a user can obtain a list of items within the storage area and the shelf-life status of each item while at the grocery store.

Returning to FIGS. 2 and 4, in an embodiment, the system 10 can include a single type of UV source 12 that is capable of operating in both operating configurations 50A, 50B. For example, the system 10 can include a type of UV source 12 that can operate in the high intensity level for the sterilization operating configuration 50A in order to sterilize microorganisms, such as bacteria, protozoa, and/or the like, and also operate in the low intensity level for the preservation operating configuration 50B in order to prevent the microorganisms, such as bacteria, protozoa, and/or the like, from growing and reproducing. The computer system 20 can be capable of adjusting the relative intensities, time durations, and/or time schedules of the UV sources 12 to correspond to these operating configurations 50.

Figure 9:
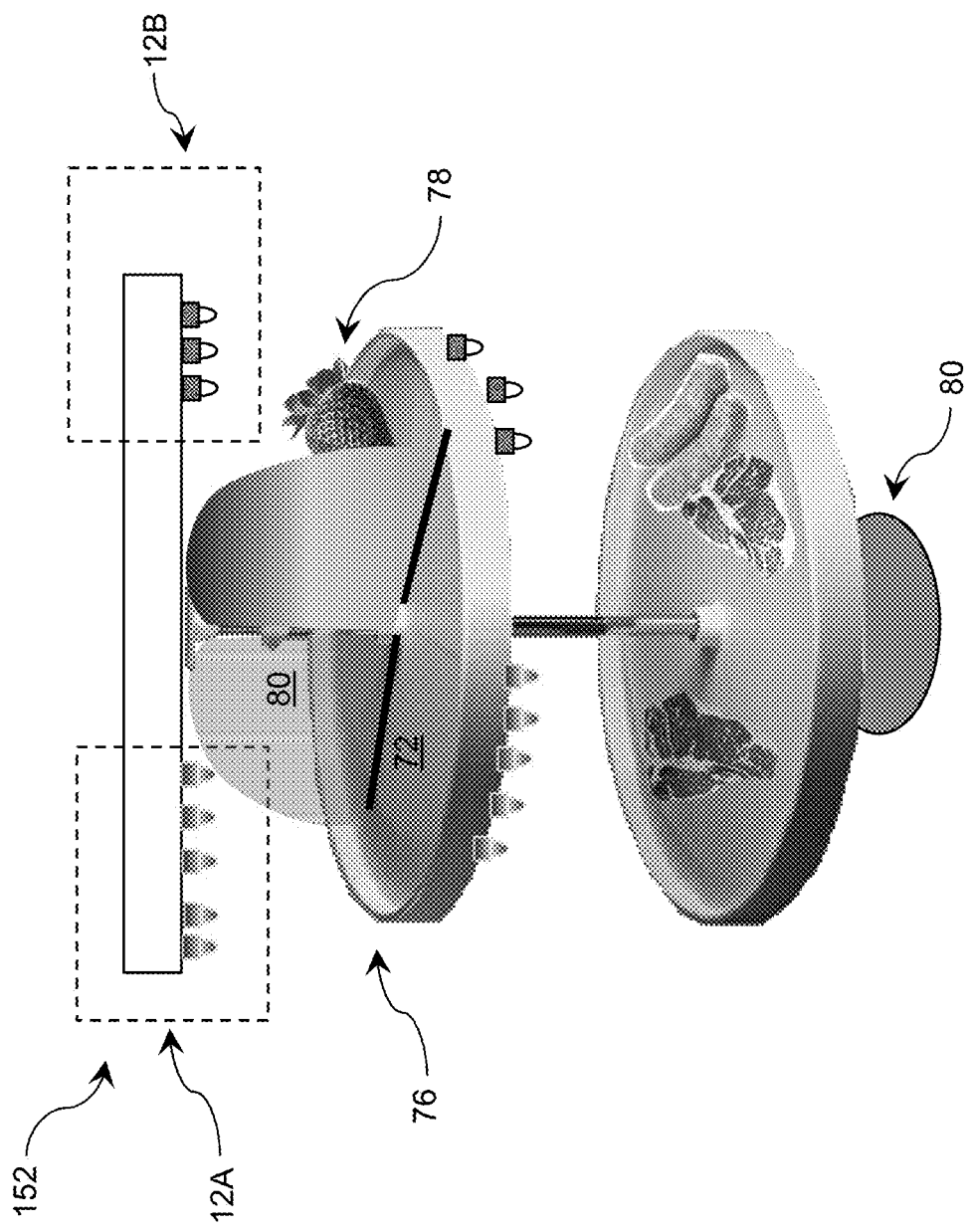
FIG. 9 shows a perspective view of an illustrative storage device according to an embodiment.

In another embodiment, the system 10 can include at least two types of UV sources 12. Referring now to FIG. 9, a perspective view of an illustrative storage device 152 according to an embodiment is shown. The storage device 152 includes a first set of UV sources 12A and a second set of UV sources 12B. The first set of UV sources 12A can be configured to operate in a first operating configuration, such as the sterilization operating configuration 50A, while the second set of UV sources 12B can be configured to operate in a second operating configuration, such as the preservation operating configuration 50B, or vice versa.

The storage device 152 can include a plurality of sub-compartments that are individually monitored by the feedback component 14 (FIG. 1). The ultraviolet radiation sources 12 in each sub-compartment can be individually controlled by the computer system 20. For example, a shelf 72 can be partitioned into a first sub-compartment 76 and a second sub-compartment 78, which are separated by a divider 80. The computer system 20 can control the UV source 12A to have a first intensity and a first wavelength, and control the UV source 12B to have a second intensity and a second wavelength. For example, the UV source 12A can include a full intensity, while the UV source 12B includes a zero intensity. Conversely, the UV source 12A can include a zero intensity, while the UV source 12B includes a full intensity. Furthermore, the computer system 20 can independently tune the relative intensities of each UV source 12A, 12B, and either UV source 12A, 12B can have any intensity between zero and full.

Figure 5B:
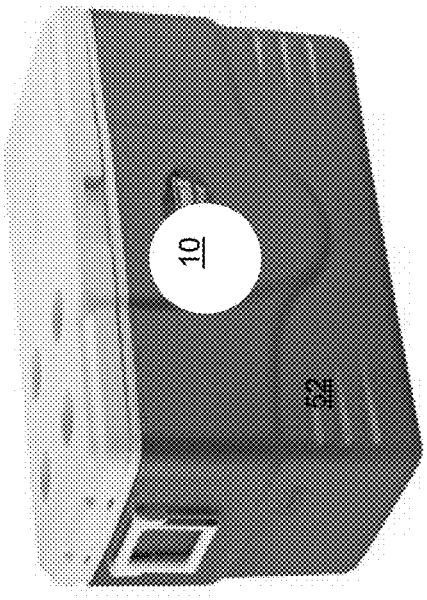
FIGS. 5A-5C show illustrative storage devices for use with an ultraviolet radiation system according to embodiments.
Figure 5C:
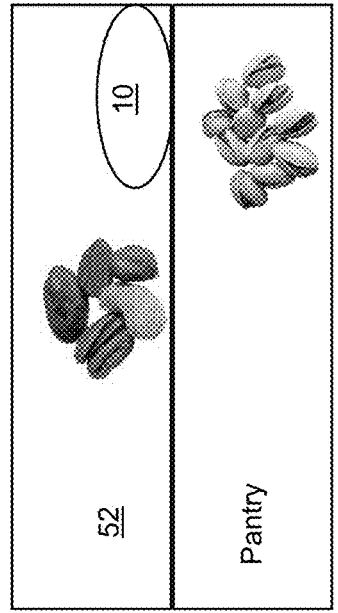
Figure 5A:
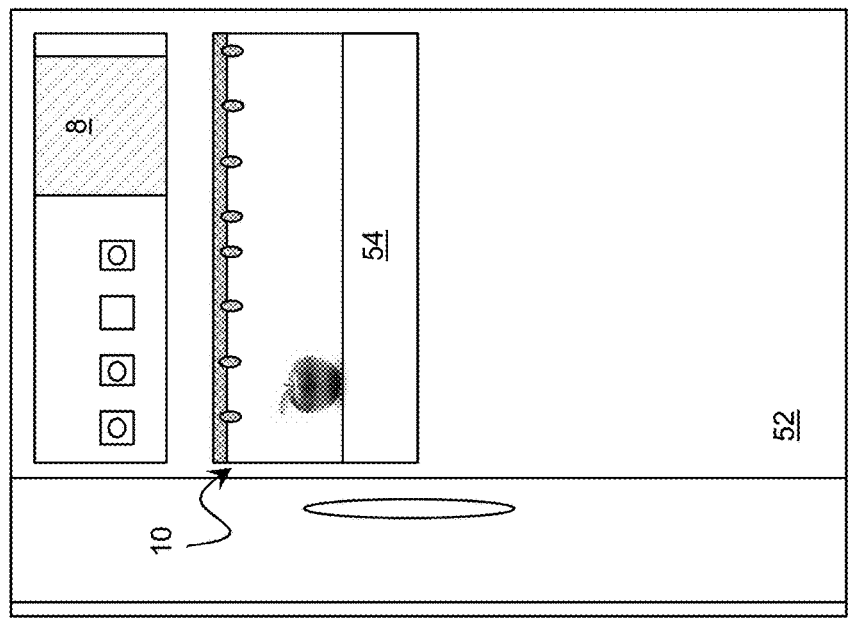
Figure 6C:
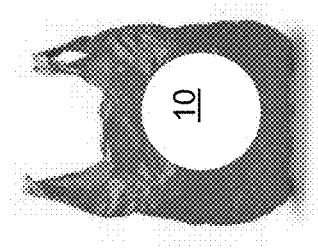
FIGS. 6A-6F show illustrative storage devices for use with an ultraviolet radiation system according to embodiments.
Figure 6F:
Figure 6B:
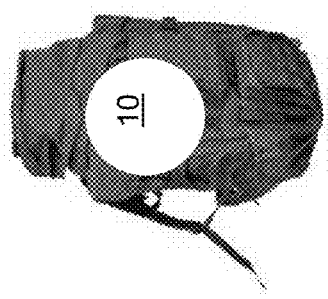
Figure 6E:
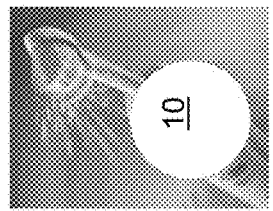
Figure 6A:
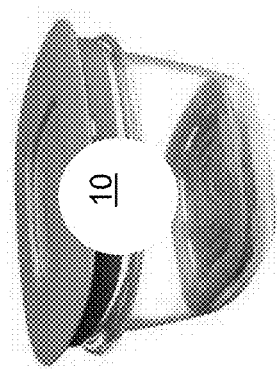
Figure 6D:
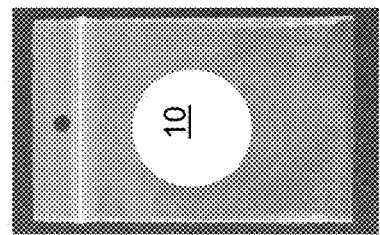
Figure 7A:
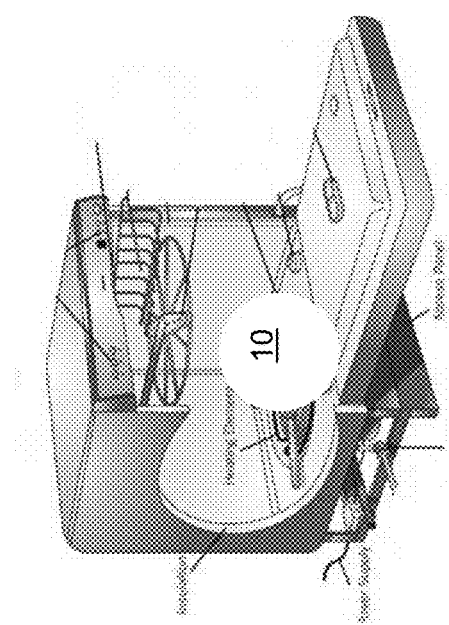
FIGS. 7A and 7B show illustrative storage devices for use with an ultraviolet radiation system according to embodiments.
Figure 7B:

As described herein, embodiments can be implemented as part of any of various types of storage systems. FIGS. 5A-5C, 6A-6F, 7A-7B, and 8A-8E show illustrative storage devices for use with an ultraviolet radiation system 10 (FIG. 1) according to embodiments. For example, the storage device can be a refrigerator and/or freezer (FIG. 5A) for storing a plurality of food items. In this embodiment, the computer system 20 can be configured to turn off UV source 12 when a door is open, and automatically turn on UV source 12 when the door is closed. Alternatively, the system 10 can be implemented in a cooler (FIG. 5B). The system 10 can be implemented in a pantry (FIG. 5C, e.g., a shelf in the pantry), and/or the like. The system 10 can be implemented in a food storage container (FIG. 6A), a backpack (FIG. 6B), a grocery bag (FIG. 6C), or a plastic baggie (FIG. 6D). In an alternative embodiment, system 10 may be utilized with an electronic toothbrush (FIG. 6E) or with a mobile touch screen phone (FIG. 6F). The system 10 can also be implemented in a dishwasher (FIG. 7A), or a sushi bar (FIG. 7B). Further, system 10 can be implemented in storage device (FIG. 8A), a vacuum cleaner (FIG. 8B), a floor cleaning robot (FIG. 8C), a floor cleaning machine (FIG. 8D), or a pc tablet case (FIG. 8E). In each case, an embodiment of the system 10 can be implemented in conjunction therewith using any solution. To this extent, it is understood that embodiments of the system 10 can vary significantly in the number of devices, the size of the devices, the power requirements for the system, and/or the like. Regardless, it is understood that these are only exemplary storage devices and that the system 10 may be applicable to other storage devices not specifically mentioned herein.

Returning to FIG. 3, it is understood that the system 10 may include a power component 19 that is implemented separately from the storage device 52 to supply power to one or more of the various components of system 10, such as ultraviolet radiation sources 12, feedback component 14, computer system 20, and/or the like. For example, the storage device 52 may comprise a cooler or the like, which does not include or otherwise require any power source. Furthermore, the storage device 52 may comprise a power source that is insufficient to operate the various devices of system 10 in addition to maintaining one or more aspects of the environment within the storage area 54 for a desired period of time. Regardless, the power component 19 can be utilized to operate system 10. The power component 19 can comprise any source of power including, but not limited to, the power grid, a battery set, an automotive charger, a solar cell, and/or the like. In an embodiment, the computer system 20 can implement multiple modes of operation depending on the source of power. In particular, when a power component 19 of limited capacity is being utilized, one or more functions of system 10 can be disabled and/or reduced to lengthen an operating time for system 10. For example, use of ultraviolet radiation source 12 to prolong the life of items within the storage area 54 or disinfect the storage area 54 by generating a higher intensity of ultraviolet radiation can be disabled.

An environment within the storage area 54 can be controlled by an environmental control component 18. In an illustrative implementation, the environmental control component 18 can comprise a temperature control module, a humidity control module, and/or a convection control module. During normal operation of the environmental control component 18, a user 6 (FIG. 1) (e.g., using external interface component 26B) can select a desired temperature, humidity, and/or the like, to maintain within storage area 54. The environmental control component 18 can subsequently operate one or more cooling/heating components of temperature control module to maintain the desired temperature, operate one or more humidifying/dehumidifying components of humidity control module to maintain the desired humidity, operate one or more air or fluid convection components (e.g., fan, pump, vent, valve, etc.) of convection control module to assist in maintaining a relatively even temperature/humidity within storage area 54, and/or the like. Alternatively, local temperature control within storage area 54 can be maintained by cool air recirculation that is controlled by the environmental control component 18.

The computer system 20 can be configured to adjust one or more operating parameters of the environmental control component 18 based on a set of current conditions in the storage area 54 and/or an operating configuration 50 of the UV radiation source 12. For example, the computer system 20 can adjust one or more of: a temperature, a humidity, a gas convection, and/or a fluid convection of the storage area 54 in response to a set of biological activity dynamics and according to a currently selected operating configuration. To this extent, each operating configuration can further define a set of target environmental conditions for use during the UV illumination. Such environmental conditions can include a target temperature, a target humidity, additional illumination by non-ultraviolet sources (e.g., visible, infrared), air circulation, and/or the like. Furthermore, one or more of the environmental conditions can change over time during implementation of the operating configuration. In an illustrative embodiment, the computer system 20 can operate the environmental control component 18 to circulate air into a chamber 60. The chamber 60 may be a source of ethylene or other gas and the computer system 20 can control chamber 60 to calibrate exposure of stored articles to such gas. The storage area 52 can also include catalysts 62 for enhancing the suppression of the biological activity, such as, titanium dioxide. Furthermore, the set of current conditions in the storage area 54 can include an operating condition of one or more components of the system 10, such as the ultraviolet radiation source(s) 12. Information regarding the operating condition can be used to, for example, notify a user 6 of a problem using the alarm component 23, alter one or more aspects of an operating configuration, and/or the like. Additionally, the set of current conditions in the storage area 54 can include data corresponding to a dose of ultraviolet radiation delivered by an ultraviolet radiation source 12 during a predetermined time period. In this case, the computer system 20 can dynamically determine when to turn off the ultraviolet radiation source 12.

As discussed herein, the computer system 20 can adjust one or more of a location/area, direction, pattern, and/or the like, of ultraviolet radiation emitted by an ultraviolet radiation source 12. To this extent, an embodiment of the ultraviolet radiation source 12 can comprise a movable ultraviolet radiation source 12, which includes one or more components operable by the computer system 20 to redirect the emitted radiation to a particular location/area, in a particular direction, in a particular pattern, and/or the like, within the storage area.

Figure 10:
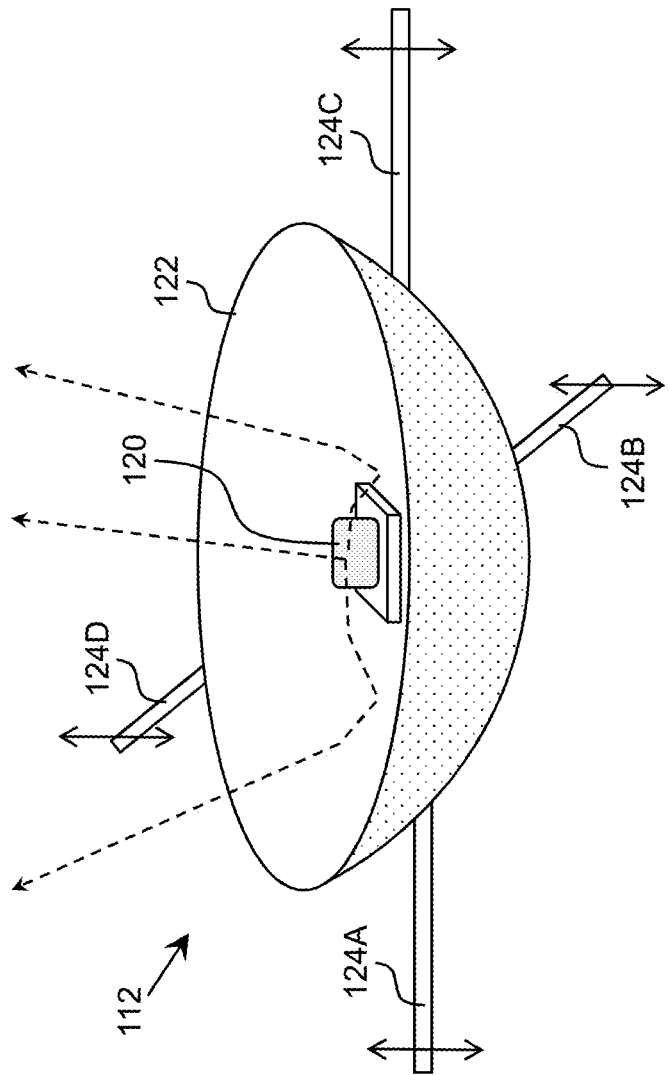
FIG. 10 shows an illustrative ultraviolet radiation source according to an embodiment.

FIG. 10 shows an illustrative ultraviolet radiation source 112 according to an embodiment. In this case, the ultraviolet radiation source 112 includes an ultraviolet emitting device 120 (e.g., ultraviolet LED, ultraviolet laser diode, and/or the like) positioned with respect to an optical element 122. The optical element 122 can comprise any type of structure, which is configured to redirect, focus, and/or the like, ultraviolet radiation emitted by the ultraviolet emitting device 120. For example, as illustrated, the optical element 122 can comprise a reflective parabolic mirror. However, it is understood that other types of optical elements can be utilized including for example, a flat parabolic mirror, a shaped ultraviolet transparent encapsulating layer (e.g., an inverted truncated conical shape), and/or the like.

One or more of the components of the ultraviolet radiation source 112 can be relocated and/or rotated by the computer system 20 (FIG. 1) to adjust a direction, focus, and/or the like, of the ultraviolet radiation emitted by the ultraviolet radiation source 112. To this extent, the ultraviolet emitting device 120 and optical element 122 can be mounted in a manner that allows relative movement between the ultraviolet emitting device 120 and optical element 122. Additionally, a mounting structure can be utilized to enable relocation and/or rotation of both the ultraviolet emitting device 120 and optical element 122.

In an embodiment, the ultraviolet radiation source 112 includes a Micro-Electro-Mechanical Systems (MEMS) mounting structure, which the computer system 20 can activate by various electronic mechanisms, to result in rotation of the optical component with such rotation having at least two degrees of freedom. For example, the ultraviolet radiation source 112 can include a MEMS mounting structure comprising elements 124A-124D, each of which can be operated by the computer system 20 to move in an up or down direction over a particular range of motion as indicated by the corresponding directional arrows. The computer system 20 can induce the motion by, for example, altering electrostatic forces such as in the case of comb-drives. The motion of each element 124A-124D can be synchronized to result in overall tilting of the optical element 122 and ultraviolet emitting device 120 mounted thereto in order to redirect the ultraviolet radiation emitted from the ultraviolet radiation source 112 to a desired location/direction. For instance, the up motion of element 124A combined with a down motion of element 124C can result in a clockwise tilting of the optical element 122. It is understood that due to constraints exerted on the motions of the elements 124A-124D, there are corresponding constraints on the tilt angle of the optical element 122.

FIGS. 11A and 11B show illustrative ultraviolet radiation sources 212A, 212B according to additional embodiments. In FIG. 11A, the ultraviolet radiation source 212A includes an ultraviolet emitting device 220 mounted to an optical element 222. The optical element 222 can comprise a reflective element, such as a polished aluminum layer, adjacent to the ultraviolet emitting device 220. The aluminum layer can be mounted over a substrate, such as an iron layer. Additionally, the ultraviolet radiation source 212A can include a MEMS mounting structure comprising a mounting element 224, such as a layer of copper, having a thermal expansion coefficient significantly different than that of the optical element 222. The optical element 222 can be solidly connected to the mounting element 224, and the elements 222, 224 can be capable of changing curvature due to a non-uniform thermal expansion of the materials forming the elements 222, 224. During operation of the ultraviolet radiation source 212A, the computer system 20 (FIG. 1) can adjust an amount of bending of the optical element 222 and mounting element 224 by thermally activating the optical element 222 and/or the mounting element 224. For example, the computer system 20 can adjust an amount of current applied through the leads 226A-226D, to create a desired amount of mechanical displacement (bending) in the optical element 222.

In FIG. 11B, the ultraviolet radiation source 212B includes multiple ultraviolet emitting devices 220A, 220B located in different positions on a bendable optical element 222 (e.g., a polished aluminum layer formed on a substrate). In this case, the computer system 20 can induce a desired amount of bending in the optical element 222 by moving one or more of the actuators 224A-224C in the directions shown. As illustrated, the bending can result in the ultraviolet radiation emitted by the ultraviolet emitting devices 220A, 220B to converge on a particular point. Additionally, the computer system 20 can selectively operate only one of the ultraviolet emitting devices 220A, 220B and use the bending to adjust a location of the ultraviolet light emitted therefrom.

It is understood that the ultraviolet radiation sources shown and described herein are only illustrative of various configurations of relocatable and/or movable ultraviolet radiation sources. For example, the solution for inducing bending shown in FIG. 11A can be implemented in conjunction with multiple ultraviolet emitting devices as shown in FIG. 11B. Similarly, the bending solution illustrated in FIG. 11B can be implemented in conjunction with a single ultraviolet emitting device as shown in FIG. 11A. Additionally, it is understood that piezoelectric actuators can be implemented in an ultraviolet radiation source to change a position and/or curvature of an optical element, change a position of an ultraviolet emitting device relative to an optical element, and/or the like.

Figure 12:
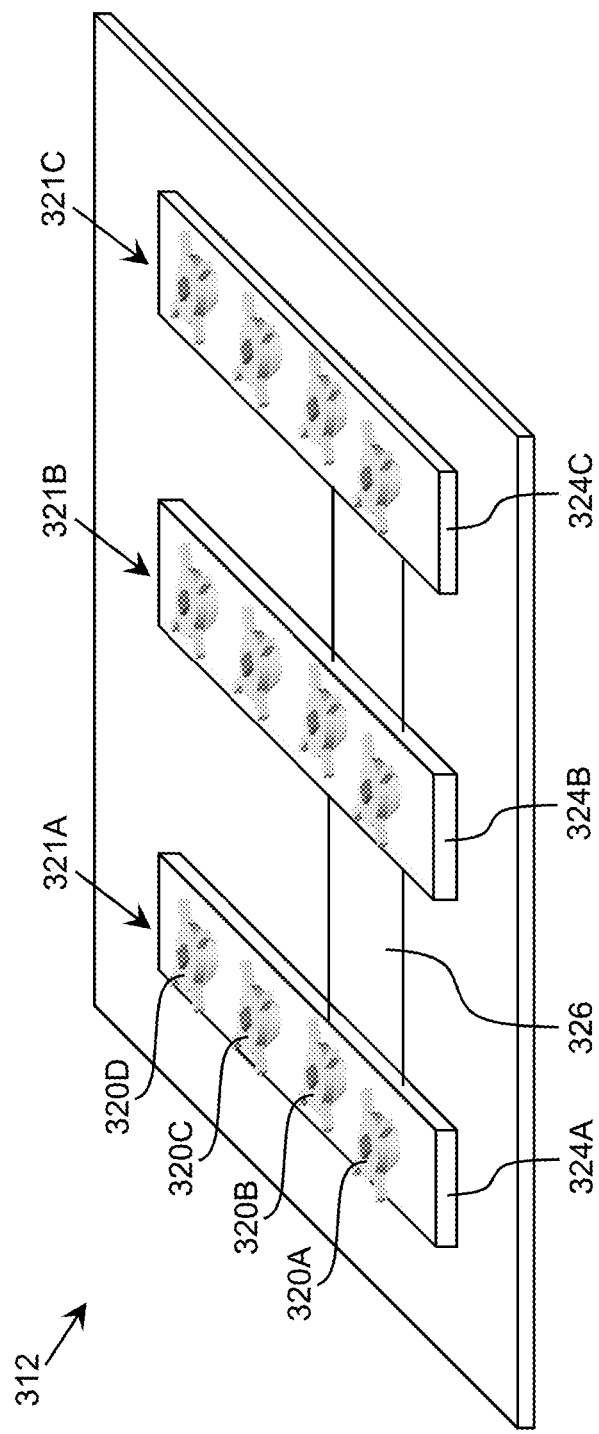
FIG. 12 shows an illustrative ultraviolet radiation source according to another embodiment.

FIG. 12 shows an illustrative ultraviolet radiation source 312 according to another embodiment. In this case, the ultraviolet radiation source 312 includes a plurality of ultraviolet emitting devices 320A-320D arranged in multiple groups 321A-321C, where each group 321A-321C is mounted to a corresponding mounting element 324A-324C. In an embodiment, the computer system 20 (FIG. 1) can selectively operate each individual ultraviolet emitting device 320A-320D in each group 321A-321C. Furthermore, the computer system 20 can adjust a direction of light emitted by the ultraviolet emitting device(s) 320A-320D. For example, a mounting element 324A-324C can be bendable and include an optical element as described herein. Furthermore, the mounting elements 324A-324C can be mounted to an actuator 326, which can enable relocation of each individual mounting element 324A-324C in a horizontal direction.

In an embodiment, the ultraviolet radiation source 312 can be utilized by the computer system 20 to generate ultraviolet radiation of varying directions, intensity, and/or wavelengths. For example, a group 321A-321C can include ultraviolet emitting devices 320A-320D that emit ultraviolet radiation at different peak frequencies. Additionally, each group 321A-321C can include ultraviolet emitting devices 320A-320D that emit ultraviolet radiation at the same peak frequency, but the different groups 321A-321C can include ultraviolet emitting devices 320A-320D that emit ultraviolet radiation of different peak frequencies from that of the other groups 321A-321C. In an embodiment, the computer system 20 can selectively: turn on or off one or more ultraviolet emitting devices 320A-320D in one or more of the groups 321A-321C; relocate and/or rotate one or more of the groups 321A-321C; and/or the like, based on a location requiring treatment and/or a type of treatment required. For example, the computer system 20 can process data acquired from a visible sensor (such as visible camera) to determine a state of the articles. In response to determining an article requires treatment (e.g., disinfection), the computer system 20 can activate the corresponding ultraviolet emitting devices 320A-320D as well as adjust the location and/or shape of the corresponding mounting element 324A-324C to deliver an appropriate dose of ultraviolet radiation to an area of the surface of the article requiring treatment.

In an embodiment, the ultraviolet emitting devices 320A-320D emit at multiple, different peak emission wavelengths. For example, the peak emission wavelengths can be separated by at least two peak half widths of the ultraviolet emitting devices 320A-320D, where a peak half width is no greater than thirty nanometers. In a more particular illustrative embodiment, a first group, such as the group 321A, can include ultraviolet emitting devices 320A-320D the computer system 20 can operate for disinfection, e.g., that emit ultraviolet radiation at a peak frequency of approximately 275 nm. Another group, such as the group 322B, can include ultraviolet emitting devices 320A-320D the computer system 20 can operate for preservation, e.g., that emit ultraviolet radiation at a peak frequency of approximately 320 nm (which can increase antioxidant components in a food article). A third group, such as the group 322C, can include ultraviolet emitting devices 320A-320D the computer system 20 can operate for disinfection of different types of bacteria and/or viruses, each of which may require ultraviolet radiation of a different peak frequency.

As described herein, aspects of the invention can be implemented to treat (e.g., preserve, disinfect, and/or the like) various types of food stored in various types of environments. A typical environment can comprise a refrigerated environment, in which food is frequently stored to extend the shelf life of the food. However, embodiments can be implemented in other non-refrigerated environments, in which food is stored for a period of time, e.g., to ripen, prior to being used, and/or the like. Furthermore, an embodiment can be implemented in conjunction with a freezer, in which the temperature is maintained well below the freezing point of water. To this extent, the types of food items to which aspects of the invention can be implemented can include various types of food as described herein. As described herein, the foods can include various types of fruits and vegetables. However, the foods also can include frozen consumables, such as ice cubes, ice cream, and/or the like. Furthermore, the foods can include liquids, grains, cereals, and/or the like. Additionally, as described herein, embodiments can be implemented to treat non-food items stored in any type of environment. Such non-food items can include, for example, frozen/liquid chemicals, sand, wood, and/or the like. Regardless, it is understood that a treated item can be ultraviolet transparent (e.g., semi-transparent), ultraviolet absorbing, and/or ultraviolet reflective.

While shown and described herein as a method and system for managing a storage area, it is understood that aspects of the invention further provide various alternative embodiments. For example, in one embodiment, the invention provides a computer program fixed in at least one computer-readable medium, which when executed, enables a computer system to manage the storage area using a process described herein. To this extent, the computer-readable medium includes program code, such as the analysis program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for managing the storage area. In this case, the generating can include configuring a computer system, such as the computer system 20 (FIG. 1), to implement a method of managing the storage area as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
    a set of ultraviolet radiation sources configured to generate ultraviolet radiation directed within a storage;
    an external interface configured to receive an input from a user;

a feedback component including at least one camera configured to monitor a set of current conditions of at least one of: the storage area or a set of items located in the storage area, the at least one camera including a visual camera and a fluorescent optical camera; and a control system including means for monitoring and controlling the set of ultraviolet radiation sources by:
monitoring, using data received from the visual camera and the fluorescent optical camera, a set of current conditions of at least one of: the storage area or a set of items located in the storage area, wherein the set of current conditions includes a change in color and a presence of bacteria and/or viruses;
receiving an input from the user via the external interface; and
controlling ultraviolet radiation generated by the set of ultraviolet radiation sources using the set of current conditions and the input from the user, wherein the controlling includes adjusting at least one of: a location within the storage area to which the ultraviolet radiation is directed, a direction of the ultraviolet radiation, a time scheduling of the ultraviolet radiation, a radiation wavelength of the ultraviolet radiation, an intensity of the ultraviolet radiation, or a pattern of the ultraviolet radiation.

2. The system of claim 1, wherein the monitoring includes detecting each item in the set of items located in the storage area.

3. The system of claim 2, the means for monitoring and controlling further comprising adjusting the ultraviolet radiation based on the detection.

4. The system of claim 1, the means for monitoring and controlling further comprising adjusting the ultraviolet radiation based on the detection, and wherein the information includes at least one of: a name for each item in the set of items, a location of each item located in the storage area, a history of ultraviolet radiation treatment for each item, and a status of each item.

5. The system of claim 4, wherein the information includes a visual representation of each item located in the storage area.

6. The system of claim 5, wherein the visual representation of each item is in real-time.

7. The system of claim 1, wherein the storage area is divided into a plurality of regions, each region including a set of ultraviolet radiation sources that are separately controlled by the control system.

8. A food storage device comprising:
a storage area configured to store a set of items;
a set of ultraviolet radiation sources configured to generate ultraviolet radiation directed within the storage area;
an external interface configured to receive an input from a user;
a feedback component including at least one camera configured to monitor a set of current conditions of at least one of: the storage area or a set of items located in the storage area, the at least one camera including a visual camera and a fluorescent optical camera; and
a control system including means for monitoring and controlling the set of ultraviolet radiation sources by:
monitoring, using data received from the visual camera and the fluorescent optical camera, a set of current conditions of at least one of: the storage area or a set of items located in the storage area, wherein the set of current conditions includes a change in color and a presence of bacteria and/or viruses;
receiving an input from the user via the external interface; and
controlling ultraviolet radiation generated by the set of ultraviolet radiation sources using the set of current conditions and the input from the user, wherein the controlling includes adjusting at least one of: a location within the storage area to which the ultraviolet radiation is directed, a direction of the ultraviolet radiation, a time scheduling of the ultraviolet radiation, a radiation wavelength of the ultraviolet radiation, an intensity of the ultraviolet radiation, or a pattern of the ultraviolet radiation.

9. The device of claim 8, wherein the monitoring includes detecting each item in the set of items located in the storage area.

10. The device of claim 9, the means for monitoring and controlling further comprising adjusting the ultraviolet radiation based on the detection.

11. The device of claim 8, the means for monitoring and controlling further comprising displaying information to the user, and wherein the information includes at least one of: a name for each item in the set of items, a location of each item located in the storage area, a history of ultraviolet radiation treatment for each item, and a status of each item.

12. The device of claim 11, wherein the information includes a visual representation of each item located in the storage area.

13. The device of claim 12, wherein the visual representation of each item is in real-time.

14. The device of claim 8, wherein the storage area is divided into a plurality of regions, each region including a set of ultraviolet radiation sources that are separately controlled by the control system.

15. A refrigeration device comprising:
a storage area configured to store at least one refrigerated item;
a component configured to control at least one environmental condition of the storage area, wherein the at least one environmental condition includes at least one of: a temperature, a humidity, a gas convection, or a fluid convection;
a set of ultraviolet radiation sources configured to generate ultraviolet radiation directed within the storage area;
an external interface configured to receive an input from a user;
a feedback component including at least one camera configured to monitor a set of current conditions of at least one of: the storage area or a set of items located in the storage area, the at least one camera including a visual camera and a fluorescent optical camera; and
a control system including means for monitoring and controlling the set of ultraviolet radiation sources by:
monitoring, using data received from the visual camera and the fluorescent optical camera, a set of current conditions of at least one of: the storage area or a set of items located in the storage area, wherein the set of current conditions includes a change in color and a presence of bacteria and/or viruses;
receiving an input from the user via the external interface; and
controlling ultraviolet radiation generated by the set of ultraviolet radiation sources using the set of current conditions and the input from the user, wherein the controlling includes adjusting at least one of: a location within the storage area to which the ultraviolet radiation is directed, a direction of the ultraviolet radiation, a time scheduling of the ultraviolet radiation, a radiation wavelength of the ultraviolet radiation, an intensity of the ultraviolet radiation, or a pattern of the ultraviolet radiation.

16. The device of claim 15, wherein the monitoring includes detecting each item in the set of items located in the storage area.

17. The device of claim 16, means for monitoring and controlling further comprising adjusting the ultraviolet radiation based on the detection.

18. The device of claim 15, the means for monitoring and controlling further comprising adjusting the ultraviolet radiation based on the detection, and wherein the information includes at least one of: a name for each item in the set of items, a location of each item located in the storage area, a history of ultraviolet radiation treatment for each item, and a status of each item.

19. The device of claim 18, wherein the information includes a visual representation of each item located in the storage area.

20. The device of claim 19, wherein the visual representation of each item is in real-time.

* * * * *